US011001783B2

(12) United States Patent
Zhang et al.

(10) Patent No.: US 11,001,783 B2
(45) Date of Patent: May 11, 2021

(54) SYNTHESIS AND USE OF ω-HYDROXYLATED POLYUNSATURATED FATTY ACIDS

(71) Applicants: THE REGENTS OF THE UNIVERSITY OF CALIFORNIA, Oakland, CA (US); UNIVERSITY OF MASSACHUSETTS, Boston, MA (US)

(72) Inventors: Guodong Zhang, Amherst, MA (US); Bruce Hammock, Davis, CA (US); Sung Hee Hwang, Davis, CA (US); Weicang Wang, Amherst, MA (US)

(73) Assignees: The Regents of the University of California, Oakland, CA (US); University of Massachusetts, Amherst, MA (US)

( * ) Notice: Subject to any disclaimer, the term of this patent is extended or adjusted under 35 U.S.C. 154(b) by 0 days.

(21) Appl. No.: 16/867,237

(22) Filed: May 5, 2020

(65) Prior Publication Data

US 2020/0332224 A1 Oct. 22, 2020

Related U.S. Application Data

(63) Continuation of application No. 16/275,293, filed as application No. PCT/US2017/047113 on Aug. 16, 2017, now Pat. No. 10,689,595.

(60) Provisional application No. 62/375,526, filed on Aug. 16, 2016.

(51) Int. Cl.

| | |
|---|---|
| ***A61P 35/00*** | (2006.01) |
| ***C11C 3/12*** | (2006.01) |
| ***C11C 3/14*** | (2006.01) |
| ***C07C 67/343*** | (2006.01) |
| ***C07C 67/303*** | (2006.01) |
| ***C07C 51/09*** | (2006.01) |

(52) U.S. Cl.
CPC .............. *C11C 3/126* (2013.01); *A61P 35/00* (2018.01); *C07C 51/09* (2013.01); *C07C 67/303* (2013.01); *C07C 67/343* (2013.01); *C11C 3/14* (2013.01)

(58) Field of Classification Search
CPC ........................................................ A61P 35/00
See application file for complete search history.

(56) References Cited

U.S. PATENT DOCUMENTS

| | | | |
|---|---|---|---|
| 8,202,893 B2 | 6/2012 | Makriyannis et al. | |
| 2014/0336397 A1 | 11/2014 | Khan et al. | |

FOREIGN PATENT DOCUMENTS

| | | | |
|---|---|---|---|
| WO | WO-2017015660 A1 * | 1/2017 | ......... G01N 33/5079 |

OTHER PUBLICATIONS

Hwang et al., "Chemical synthesis and biological evaluation of w-hydroxy polyunsaturated fatty acids", Bioorganic & Medicinal Chemistry Letter, Dec. 2, 2016, vol. 27, Iss. 3, Abstract.
International Search Report for PCT/US2017/047113 dated Oct. 25, 2017.
Reber, "New efficient methods for the preparation of natural product derivatives", Swiss Federal Institute of Technology ETH Zurich, D. Sc. Dissertation 2007, Abstract.
Wang et al., "w-3 polyunsaturated fatty acids-derived lipid metabolites on angiogenesis, inflammation and cancer", Prostaglandins and other Lipid Mediators, Jul. 11, 2014, pp. 13-20, vol. 113-115.

* cited by examiner

*Primary Examiner* — Joseph R Kosack
(74) *Attorney, Agent, or Firm* — Mintz Levin Cohn Ferris Glovsky and Popeo, P.C.

(57) ABSTRACT

The present invention provides a synthetic chemical method for preparing ω-hydroxylated polyunsaturated fatty acids (PUFAs) including 20-hydroxyeicosatetraenoic acid (20-HETE), 20-hydroxyeicosapentaenoic acid (20-HEPE), and 22-hydroxydocosahexaenoic acid (22-HDoHE) and a method of use thereof for treating cancer and macular degeneration.

2 Claims, 12 Drawing Sheets

Docosahexaenoic acid (DHA)

22-hydroxydocosahexaenoic acid (22-HDoHE)

Control 1 μM 22-HDoHE 3 μM 22-HDoHE

Control 1 μM 22-HDoHE 3 μM 22-HDoHE

SYNTHESIS AND USE OF ω-HYDROXYLATED POLYUNSATURATED FATTY ACIDS

CROSS-REFERENCES TO RELATED APPLICATIONS

This application is a continuation of U.S. application Ser. No. 16/275,293, filed on Feb. 13, 2019, which is the national phase under 35 U.S.C. § 371 of International Application No. PCT/US2017/047113, filed on Aug. 16, 2017, which claims priority benefit to U.S. Provisional Application No. 62/375,526, filed on Aug. 16, 2016, the entirety of which are incorporated herein by reference for all purpose.

STATEMENT AS TO RIGHTS TO INVENTIONS MADE UNDER FEDERALLY SPONSORED RESEARCH AND DEVELOPMENT

This invention was made with government support under NIEHS grant R01 ES02710, NIEHS Superfund Basic Research Program grant P42 ES04699, NIHLB grant HL059699 and NINDS grant U54 NS079202. The government has certain rights in the invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Polyunsaturated fatty acids (PUFAs) are metabolized by CYP450 enzymes that function as monooxygenases mainly by catalyzing hydroxylation and epoxidation (see Ref 1). Arachidonic acid (ARA) is metabolized by the CYP450s to hydroxyeicosatetraenoic acids (HETEs) and epoxyeicosatrienoic acids (EETs). While all EET isomers are almost equally formed, 20-hydroxyeicosatetraenoic acid (20-HETE), a product by w-hydroxylation, is major HETE regioisomer derived from ARA. These metabolites are important lipid mediators that play important roles in various diseases (see Ref. 2). Interestingly, EETs and HETEs often have opposing biological functions (see Ref. 2).

Every CYP450 produces both EETs and HETEs. However, epoxygenases, such as CYP2C and CYP2J isoforms, produce mostly epoxides, and hydroxylases, such as CYP4A and CYP4F isoforms, produce mostly 20-HETE. The same CYP isoforms also metabolize ω-3-polyunsaturated fatty acids such as eicosapentaenoic acid (EPA) and docosahexaenoic acid (DHA) to the corresponding epoxy- and hydroxyl polyunsaturated fatty acids (see Ref 3). Recently, beneficial effects from dietary supplements of fish oil including prescription ω-3 fish oil have triggered interests in the biological functions of their metabolites (see Ref 4). For example, it is showed that epoxides of EPA and DHA can reduce pain perception (see Ref. 5), blood pressure (see Ref. 6), and angiogenesis (see Ref. 7). Herein, the present disclosures are concentrating on the biological role of ω-hydroxy polyunsaturated fatty acid metabolites.

Biological roles of 20-HETE have been well studied, and have been shown to have detrimental effects on several diseases such as hypertension (see Ref 8), cancer (see Ref. 9), and cardiovascular and kidney diseases (see Ref 10). In addition, there is growing evidence to suggest that 20-HETE is a potent agonist of the transient receptor potential vanilloid receptor 1 (TRPV1) which is activated by endogenous lipid mediators and is closely related to pain (see Ref. 11).

However, little is known about the biological roles of other ω-hydroxylated PUFAs due mostly to their limited availability or difficulty to synthesize them. These are 20-hydroxyeicosapentaenoic acid (20-HEPE) and 22-hydroxydocosahexaenoic acid (22-HDoHE) derived from EPA and DHA respectively. 22-hydroxydocosahexaenoic acid (22-HDoHE) is an endogenous lipid mediator produced by cytochrome P450 ω-hydroxylases (largely CYP4A and CYP4F) from docosahexaenoic acid (DHA, 22:6 ω-3), as shown in FIG. 1A. It is an endogenous compound and has been detected in many tissues such as brain, lung, kidney and liver, as shown in FIG. 1B (see Ref 35).

Gopal et. al. reported a chemical synthesis of 20-HETE by a Suzuki-Miyaura cross-coupling of a cis-vinylbromide compound with a functionalized borane (see In *Tetrahedron Lett.* 2004, 45 (12), 2563-2565). Apart from that, several biosynthesis of 20-HETE have been reported (see Ref 12). Harmon et. al. reported a 20-HEPE synthesis by oxygenation of ω-3 fatty acids by human cytochrome P450 4F3B (see *Prostaglandins, leukotrienes, and essential fatty acids* 2006, 75 (3), 169-77). However, a complete synthesis of 22-HDoHE has not been reported yet.

In view of the number of possible applications for the treatment of diseases there is a need for a synthetic chemical method of preparing 22-HDoHE, 20-HEPE, and 20-HETE.

Described herein, inter alia, are solutions to these and other problems in the art.

BRIEF SUMMARY OF THE INVENTION

In one aspect, the present invention is directed to a method for preparing a compound of Formula II:

(II)

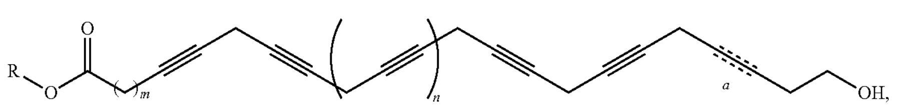

the method including:

forming a coupling reaction mixture comprising a transition-metal coupling agent, a base, a compound of Formula III:

(III)

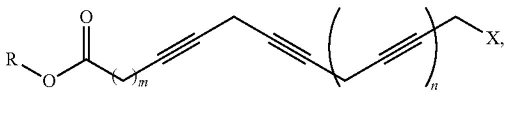

and a compound of Formula IV:

(IV)

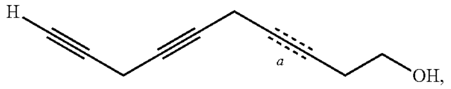

under conditions suitable to form the compound of Formula II;

wherein:

the transition-metal coupling agent comprises a metal selected from the group consisting of copper, iron, nickel, palladium, zinc, and combinations thereof;

R is $C_1$-$C_4$ alkyl;

X is selected from the group consisting of Cl, Br, I, —OTs, and —OTf;

subscript m is 2 or 3;

subscript n is 0 or 1; and bond a is a single bond or a triple bond.

In one aspect, the present invention is directed to a method for preparing a compound of Formula I:

(I)

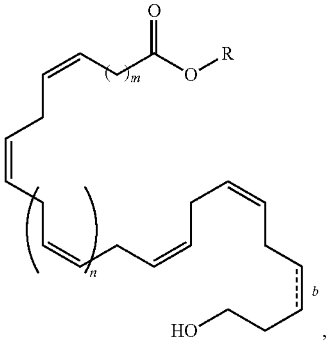

the method including:

i) forming a coupling reaction mixture comprising a transition-metal coupling agent, a base, a compound of Formula III:

(III)

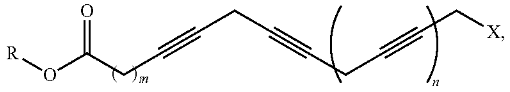

and a compound of Formula IV:

(IV)

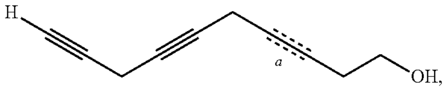

under conditions suitable to form a compound of Formula II:

(II)

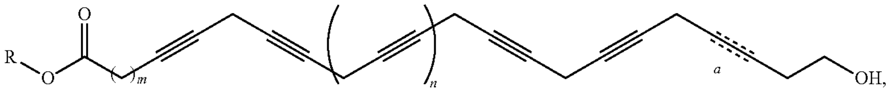

and ii) forming a hydrogenation reaction mixture comprising the compound of Formula II, a deactivated palladium catalyst, a deactivating agent, and hydrogen, under conditions suitable for hydrogenation to form the compound of Formula I;

wherein:

the transition-metal coupling agent comprises a metal selected from the group consisting of copper, iron, nickel, palladium, zinc, and combinations thereof;

R is $C_1$-$C_4$ alkyl;

X is selected from the group consisting of Cl, Br, I, —OTs, and —OTf;

subscript m is 2 or 3;

subscript n is 0 or 1; and bond a and bond b are each a single bond or bond a is a triple bond and bond b is a double bond.

In another aspect, the present invention is directed to a method of preparing a ω-hydroxylated polyunsaturated fatty acid having a structure of:

(20-HETE)

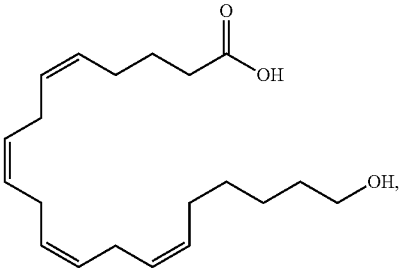

or (20-HEPE)

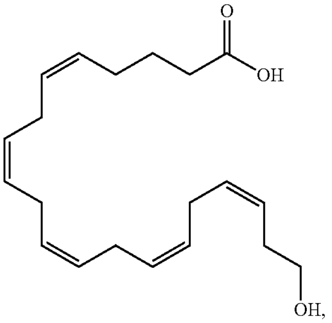

or a salt thereof;

the method including:

i) forming a coupling reaction mixture comprising a copper ion, an iodide salt, an alkali carbonate, an aprotic solvent, a compound of Formula (III-1a)

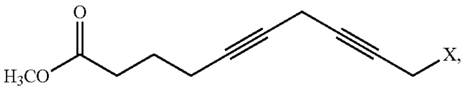

and a compound of Formula Iv-1 or Iv-2:

(IV-1)

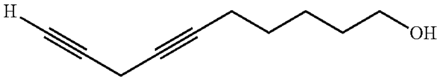

(IV-2)

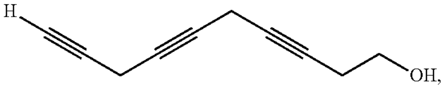

under conditions suitable to form a corresponding compound of Formula II-1a or II-2a:

(II-1a)

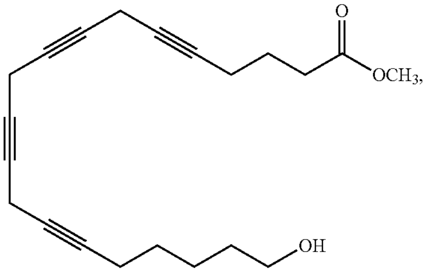

(II-2a)

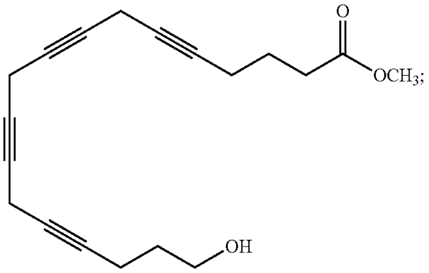

ii) forming a hydrogenation reaction mixture comprising the compound of Formula II-1a or II-2a, Lindlar catalyst, a N-containing 5- to 10-membered heteroaryl compound, a $C_2$-$C_6$ alkene, and hydrogen, under conditions suitable for hydrogenation to form a corresponding compound of Formula I-1a or I-2a:

(I-1a)

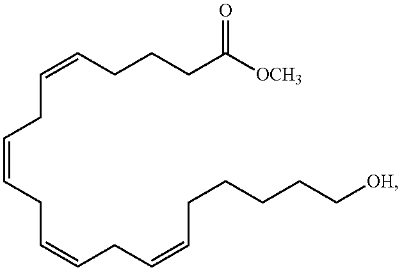

-continued (I-2a)

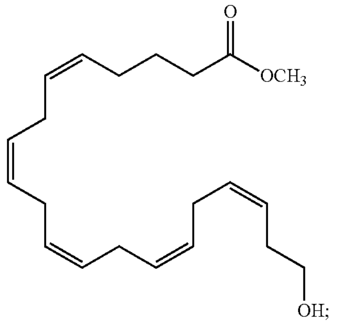

iii) forming a hydrolysis reaction mixture comprising the compound of Formula I-1a or I-2a and an alkali hydroxide under conditions suitable for saponification to form the corresponding the compound or the salt of 20-HETE or 20-HEPE;

wherein:

the copper ion is a copper (I) ion salt selected from the group consisting of CuI, CuBr, CuCl, and Cu(OAc); and X is selected from the group consisting of Cl, Br, I, and —OTs.

In another aspect, the present invention is directed to a method of preparing a ω-hydroxylated polyunsaturated fatty acid having a structure of:

(22-HDoHE)

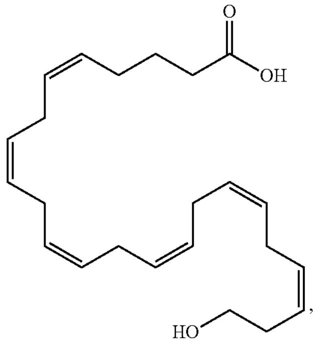

or a salt thereof;

the method includes:

i) forming a coupling reaction mixture comprising a copper ion, an iodide salt, an alkali carbonate, an aprotic solvent, a compound of Formula III-2a:

(III-2a)

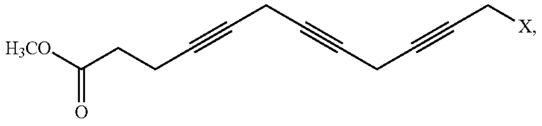

and a compound of Formula IV-2:

(IV-2)

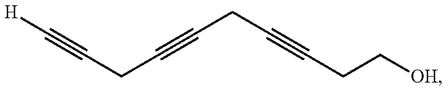

under conditions suitable to form the compound of Formula II-3a:

(II-3a)

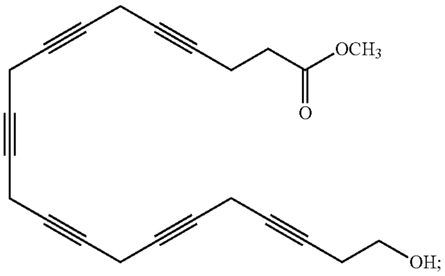

ii) forming a reaction mixture comprising a compound of Formula II-3a, Lindlar catalyst, a N-containing 5- to 10-membered heteroaryl compound, a $C_2$-$C_6$ alkene, and hydrogen, under conditions suitable for hydrogenation to form a compound of Formula I-3a:

(I-3a)

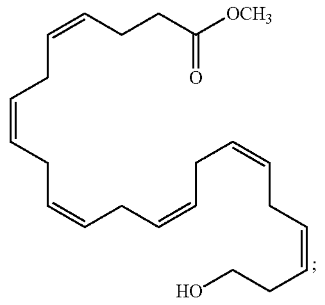

iii) forming a hydrolysis reaction mixture comprising the compound of Formula I-3a and an alkali hydroxide under conditions suitable for saponification to form the compound or the salt of 22-HdoHE;

wherein:

the copper ion is a copper (I) ion salt selected from the group consisting of CuI, CuBr, CuCl, and Cu(OAc); and X is selected from the group consisting of Cl, Br, I, and —OTs.

In still another aspect, the present invention is directed to a pharmaceutical composition including a ω-hydroxylated polyunsaturated fatty acid, or an ester form thereof, and a pharmaceutically acceptable excipient.

In yet another aspect, the present invention is directed to a method of treating cancer or macular degeneration, the method including administering to a subject in need thereof an effective amount of a ω-hydroxylated polyunsaturated fatty acid, or the ester form thereof, or a pharmaceutical composition thereof.

DETAILED DESCRIPTION OF THE INVENTION

I. General

Figure 1A:
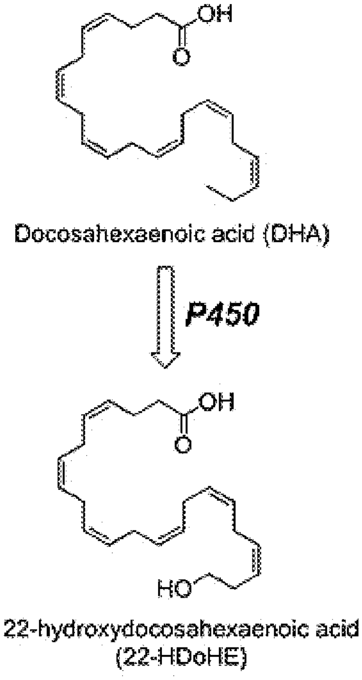
FIG. 1A shows the conversion of docosahexaenoic acid (DHA) to 22-hydroxydocosahexaenoic acid (22-HDoHE) through the metabolism catalyzed by cytochrome P450 ω-hydroxylases.
Figure 1B:
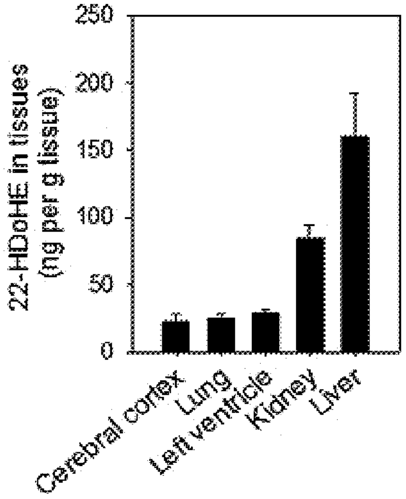
FIG. 1B is a bar graph showing the tissue levels of 22-HDoHE in mouse organs.

The present invention provides a method of preparing ω-hydroxylated polyunsaturated fatty acids (i.e., 20-HETE, 20-HEPE, and 22-HDoHE) through a convergent synthesis approach. Serial copper-mediated coupling reactions to construct skipped alkynes and their partial hydrogenation to the desired cis-double bonds of each ω-hydroxylated polyunsaturated fatty acid have been used as key reactions. The convergent synthesis minimizes time and effort since several intermediates are partially shared during the preparation of all three ω-hydroxylated polyunsaturated fatty acids. Finally, hydrolysis of the esters of 20-HETE, 20-HEPE, and 22-HDoHE has provided the desired ω-hydroxylated polyunsaturated fatty acids in good overall yields, respectively.

The present invention provides a method of using ω-hydroxylated polyunsaturated fatty acids for treatment of cancer or macular degeneration. The ω-hydroxylated polyunsaturated fatty acids, for example 22-HDoHE, have demonstrated to inhibits tumor growth, angiogenesis, lymphangiogenesis in cell culture and animal models.

II. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl" by itself or as part of another substituent, means, unless otherwise stated, a straight or branched, saturated, aliphatic radical having the number of carbon atoms indicated. (i.e., $C_1$-$C_4$ means one to four carbons). For example, $C_{1-4}$ alkyl includes, but is not limited to, methyl, ethyl, propyl, isopropyl, butyl, isobutyl, sec-butyl, and tert-butyl.

The term "alkene" is a straight chain or branched hydrocarbon having at least 2 carbon atoms and at least one double bond and having the number of carbon atoms indicated (i.e., $C_2$-$C_6$ means two to six carbons). Examples of alkenes include, but are not limited to, ethene, propene, isopropene, 1-butene, 2-butene, isobutene, butadiene, 1-pentene, 2-pentene, isopentene, 2-methyl-2-butene, 1,3-pentadiene, 1,4-pentadiene, 1-hexene, 2-hexene, 3-hexene, 1,3-hexadiene, 1,4-hexadiene, 1,5-hexadiene, 2,4-hexadiene, or 1,3,5-hexatriene.

The term "alkyne" is a straight chain or branched hydrocarbon having at least 2 carbon atoms and at least one triple bond.

"Amine" refers to a compound having formula $N(R)_3$ where the R groups can be hydrogen, alkyl, aryl, or heteroalkyl, among others. The R groups can be the same or different. For example, the amines can be primary amine (two R is each hydrogen), secondary amine (one R is hydrogen), and tertiary amine (each R is other than hydrogen). In some embodiments, the secondary amine is a cyclic amine where two R groups bond to the nitrogen atom form a 5-6 membered heterocyclic ring. Non-limiting examples of cyclic amines include pyrrolidine, piperidine, and morpholine. In other embodiments, the amine is a diamine where one of R groups is an aminoalkyl. Non-limiting examples of diamines include ethylenediamine.

"Alkyl amine" refers to an amine as defined above where the R groups are one or more alkyl groups. For example, the alkylamine can be monoalkylamine, dialkylamine or trialkylamine. Monoalkylamines useful in the present invention include, but are not limited to, ethylamine, propylamine, isopropylamine, butylamine, ethylenediamine, and ethanolamine. Dialkylamines useful in the present invention include, but are not limited to, diethylamine, dipropylamine, diisopropylamine, and dibutylamine. Trialkylamines useful in the present invention include, but are not limited to, trimethylamine, triethylamine, tripropylamine, and triisopropylamine.

The term "N-containing heteroaryl" refers to a monocyclic or fused bicyclic aromatic ring assembly containing 5 to 10 ring atoms, where at least one atom of the ring is N. The term "N-containing 5- to 10-membered heteroaryl" refers heteroaryl groups having from 5 to 10 ring members and from 1 to 3 ring atoms including N, O or S. The "N-containing 5- to 10-membered heteroaryl" compounds include, but are not limited to, pyrrole, pyridine, imidazole, pyrazole, triazole, pyrazine, pyrimidine, pyridazine, triazine (1,2,3-, 1,2,4- and 1,3,5-isomers), thiazole, isothiazole, oxazole, isoxazole, indole, isoindole, quinoline, isoquinoline, quinoxaline, quinazoline, and phthalazine. In some embodiments, the "N-containing 5- to 10-membered heteroaryl" include heteroaryl groups having from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, and phthalazine. In other embodiments, the "N-containing 5- to 10-membered heteroaryl" include heteroaryl groups having from 5 to 10 ring members and only one nitrogen heteroatom, such as pyrrole, pyridine, indole, isoindole, quinoline, and isoquinoline.

The abbreviation "—OTs" refers to p-toluenesulfonate. The abbreviation "—OTf" refers to trifluoromethanesulfonate.

The term "metal" refers to elements of the periodic table that are metallic and that can be neutral, or positively charged as a result of having more or fewer electrons in the valence shell than is present for the neutral metallic element. Metals useful in the present invention include the alkali metals and transition metals. Alkali metals in the present invention include alkali metal cations. Alkali metal cations useful in the present invention include $Li^+$, $Na^+$, $K^+$, and $Cs^+$. Transition metals useful in the present invention include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Transition metals useful in the present invention include transition metal cations, for example, $Cd^{2+}$, $Co^{2+}$, $Co^{3+}$, $Cr^{2+}$, $Cr^+$, $Cu^+$ (i.e., Cu(I)), $Cu^{2+}$, $Fe^{2+}$, $Fe^{3+}$, $Mn^{2+}$, $Mn^{3+}$, $Ni^{2+}$, $Ni^{3+}$, $Pd^{2+}$ (i.e., Pd(II)), and The term "base" refers to a functional group that deprotonates water to produce a hydroxide ion. Exemplary bases are amines as defined above, N-containing heteroaryl as defined above, or alkali carbonates. Examples of alkali carbonates include potassium carbonate, sodium carbonate, and cesium carbonate.

The term "alkali carbonate" refers to a class of chemical compounds which are composed of an alkali metal cation and the carbonate anion ($—CO_3^{2-}$). Alkali carbonates useful in the present invention include sodium carbonate ($Li_2CO_3$), sodium carbonate ($Na_2CO_3$), potassium carbonate ($K_2CO_3$), and cesium carbonate ($Cs_2CO_3$).

The term "alkali hydroxide" refers a class of chemical compounds which are composed of an alkali metal cation and the hydroxide anion ($OH^-$). Alkali hydroxides useful in the present invention include LiOH, NaOH, KOH, and CsOH.

The term "catalyst" refers to a substance that increases the rate of a chemical reaction by reducing the activation energy, but which is left unchanged by the reaction. Catalysts may be classified as either homogeneous or heterogeneous. A homogeneous catalyst is one whose molecules are dispersed in the same phase as the reactant molecules. A heterogeneous catalyst is one whose molecules are not in the same phase as the reactants, which are typically gases or liquids that are adsorbed onto the surface of the solid catalyst. Catalysts useful in the present invention are both homogeneous catalysts and heterogeneous catalysts.

The term "transition-metal coupling agent" refers to a compound that is composed of a transition metal as defined above that can be neutral, or positively charged. The transition-metal coupling agent plays a critical role in a transition metal mediated cross-coupling reaction to form a carbon-carbon bond.

The term "deactivated palladium catalyst" refers a palladium (0) catalyst that is poisoned with addition of various forms of lead and sulfur, certain metal oxides, N-containing heteroaryl compounds. Examples of "catalyst poisons" include, but are not limited to, the addition of lead acetate, lead oxide, quinolone, sulfides, thiols, or combinations thereof to the catalyst. Example of a commercial deactivated palladium catalyst is a Lindlar catalyst. The Lindlar catalyst is used for the hydrogenation of alkynes to alkenes (i.e. without further reduction into alkanes).

The term "deactivating agent" refers compounds that are used to further poison the deactivated palladium catalyst. Examples of "deactivating agent" include N-containing 5- to 10-membered heteroaryl compounds, thiols, or diamines. Non-limiting examples of N-containing 5- to 10-membered heteroaryl compounds include pyridine, picoline, lutidine, collidine, and quinoline. Non-limiting examples of thiols include 3,6-dithia-1,8-octanediol. Non-limiting examples of diamines include ethylenediamine.

The term "aprotic solvent" refers to solvents that lack an acidic hydrogen. Consequently, they are not hydrogen bond donors. Common characteristics of aprotic solvents are solvents that can accept hydrogen bonds, solvents do not have acidic hydrogen, and solvents dissolve salts. Example of aprotic solvents include, but are not limited to, N-methylpyrrolidone (NMP), tetrahydrofuran (THF), ethyl acetate (EtOAc), acetone, dimethylformamide (DMF), acetonitrile (MeCN), dimethyl sulfoxide (DMSO), propylene carbonate (PC), and hexamethylphosphoramide (HMPA).

The term "forming a reaction mixture" refers to the process of bringing into contact at least two distinct species such that they mix together and can react, either modifying one of the initial reactants or forming a third, distinct, species, a product. It should be appreciated, however, the resulting reaction product can be produced directly from a reaction between the added reagents or from an intermediate from one or more of the added reagents which can be produced in the reaction mixture.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The term "composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof.

The term "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In some embodiments, inhibition means negatively affecting (e.g. decreasing) the concentration or levels of the protein relative to the concentration or level of the protein in the absence of the inhibitor. In some embodiments, inhibition refers to reduction of a disease or symptoms of disease. In some embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In some embodiments, inhibition refers to a reduction of activity of a target protein resulting from a direct interaction (e.g. an inhibitor binds to the target protein). In other embodiments, inhibition refers to a reduction of activity of a target protein from an indirect interaction (e.g. an inhibitor binds to a protein that activates the target protein, thereby preventing target protein activation).

The terms "treat", "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In some embodiments, treating is preventing. In other embodiments, treating does not include preventing.

The term "patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Cal-*

*culations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include brain cancer, glioma, glioblastoma, neuroblastoma, prostate cancer, colorectal cancer, pancreatic cancer, cervical cancer, gastric cancer, ovarian cancer, lung cancer, and cancer of the head. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

When introducing elements of the present disclosure, the articles "a", "an", "the", and "said" are intend to mean that there are one or more of the elements. The terms "comprising", "including", and "having" are intended to be inclusive and mean that there may be additional elements other than the listed elements.

III. Method of Preparing Compounds

A. Alkynes of Formula II

In one aspect, provided herein is a method for preparing a compound of Formula II:

(II)

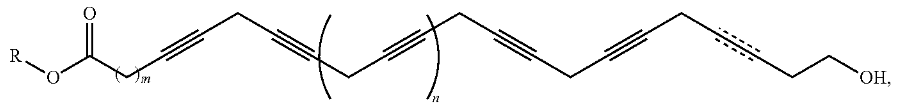

the method including:

forming a coupling reaction mixture comprising a transition-metal coupling agent, a base, a compound of Formula III:

(III)

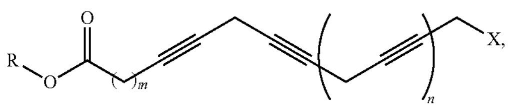

and a compound of Formula IV:

(IV)

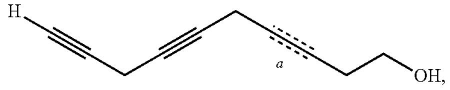

under conditions suitable to form the compound of Formula II;

wherein:

the transition-metal coupling agent comprises a metal selected from the group consisting of copper, iron, nickel, palladium, zinc, and combinations thereof;

R is $C_1$-$C_4$ alkyl;

X is selected from the group consisting of Cl, Br, I, —OTs, and —OTf;

subscript m is 2 or 3;

subscript n is 0 or 1; and bond a is a single bond or a triple bond.

Transition-metal coupling agent can be a compound that includes one or more transition metals or transition metal cations. Non-limiting examples of transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Non limiting examples of transition metal cations include $Cd^{2+}$, $Co^{2+}$, $Co^{3+}$, $Cr^{2+}$, $Cr^{3+}$, $Cu^{+}$, $Cu^{2+}$, $Fe^{2+}$, $Fe^{3+}$, $Mn^{2+}$, $Mn^{3+}$, $Ni^{2+}$, $Ni^{3+}$, $Pd^{2+}$, and $Zn^{2+}$. In some embodiments, the transition-metal coupling agent includes a metal selected from the group consisting of copper (Cu), iron (Fe), nickel (Ni), palladium (Pd), zinc (Zn), and combinations thereof.

In some embodiments, the transition-metal coupling agent includes copper. In some embodiments, the transition-metal coupling agent is copper. In some embodiments, the transition-metal coupling agent includes a copper ion. In some embodiments, the transition-metal coupling agent is a copper ion.

In some embodiments, the copper ion is a copper (I) ion.

In some embodiments, the copper (I) ion is a copper (I) salt. Non-limiting examples of the copper (I) salt include CuI, CuBr, CuCl, and Cu(OAc). In some embodiments, the copper (I) ion is a copper (I) salt selected from the group consisting of CuI, CuBr, CuCl, and Cu(OAc). In some embodiments, the copper (I) salt is CuI. In some embodiments, the copper (I) salt is CuBr. In other embodiments, the copper (I) salt is CuCl. In still other embodiments, the copper (I) salt is Cu(OAc) (i.e., copper (I) acetate).

The carbon-carbon cross coupling of the terminal alkyne of Formula (IV) with the compound of Formula (III) can also be conducted in a reaction mixture that includes a palladium catalyst, a Cu(I) ion as a ω-coupling agent, and a base. In those embodiments, the transition-metal coupling agent includes a palladium catalyst and a copper (I) ion. The palladium catalyst, for example, is a zerovalent palladium (i.e., Pd(0)) complex. Examples of such palladium catalysts include a palladium-phosphine complex in which palladium is ligated to phosphines (e.g., $Pd(PPh_3)_4$). Palladium (II) is often employed as a pre-catalyst since it exhibits greater stability than Pd(0) over an extended period of time and can be stored under normal laboratory conditions for months. The Pd(II) catalyst is reduced to Pd(0) in the reaction mixture by either an amine, a phosphine ligand, or a reactant, allowing the reaction to proceed. In some embodiments, the palladium-phosphine complex is a palladium (II)-phosphine complex. A commonly used palladium (II)-phosphate complex is $Pd(PPh_3)_2Cl_2$. In those specific embodiments, the transition-metal coupling agent includes $Pd(PPh_3)_2Cl_2$ and a copper (I) ion. Other palladium-phosphine complexes include bidentate ligand (e.g., 1,2-Bis (diphenylphosphino)ethane (dppe), 1,3-Bis(diphenylphosphino)propane (dppp), and 1,1'-Bis(diphenylphosphino) ferrocene (dppf)) palladium complexes, for example Pd(dppe)Cl and $Pd(dppp)Cl_2$, and $Pd(dppf)Cl_2$.

The transition metal coupling agent including a copper (I) ion can be present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some embodiments, the copper (I) ion is present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some embodiments, CuI is present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some other embodiments, CuI is present in the coupling reaction mixture in an amount of 1.0 molar equivalent, relative to the compound of Formula (IV).

In general, the coupling reaction can include a base in the reaction mixture. Without being bond by theory, it is believed that the base in the reaction mixture is to neutralize the hydrogen halide, p-toluenesulfonic acid, or trifluoromethanesulfonic acid that is produced as the byproduct of this coupling reaction. In some embodiments, the base is an amine or an alkali carbonate. The amines can be alkylamine compounds, for example, di-($C_1$-$C_4$ alkyl)amines and a tri-($C_1$-$C_4$ alkyl)amines. The amine can also be cyclic amines, for example, pyrrolidine, piperidine, and morpholine. In some embodiments, the base is selected from the group consisting of a di-($C_1$-$C_4$ alkyl)amine, a tri-($C_1$-$C_4$ alkyl) amine, and an alkali carbonate. Non-limiting examples of di-($C_1$-$C_4$ alkyl)amines include diethylamine, dipropylamine, diisopropylamine, and dibutylamine. Non-limiting examples of tri-($C_1$-$C_4$ alkyl)amines include trimethylamine, triethylamine, tripropylamine, and triisopropylamine. In some embodiments, the base is triethylamine. In other embodiments, the base is diethylamine. In some embodiments, the base is an alkali carbonate. The alkali carbonate can be potassium carbonate, sodium carbonate, or cesium carbonate. In some embodiments, the alkali carbonate is potassium carbonate or cesium carbonate. In other embodiments, the alkali carbonate is cesium carbonate. In some selected embodiments, the base is cesium carbonate.

The base can be present in excess in the coupling reaction mixture. In some embodiments where the base is an amine, the amine is present in excess in the coupling reaction mixture. In some embodiments, the base can be present in the coupling reaction mixture in an amount of from 0.5 to 10 molar equivalents, 0.5 to 5 molar equivalents, 1 to 2 molar equivalents, 1 to 1.5 molar equivalents, or 1.0 molar equivalent, relative to the compound of Formula (IV). In some embodiments, the alkali carbonate is present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some embodiments, cesium carbonate is present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some other embodiments, cesium carbonate is present in the coupling reaction mixture in an amount of 1.0 molar equivalent, relative to the compound of Formula (IV).

When di-($C_1$-$C_4$ alkyl)amines or tri-($C_1$-$C_4$ alkyl)amines are used as the base, they can be sometimes used as solvents. For example, triethylamine or diethylamine can be used as the solvent as well as the base in the reaction mixture for the coupling reaction.

The coupling reaction mixture further includes an iodide salt. When X is I and the copper (I) salt is CuI, an iodide salt can be optional in the reaction mixture. The iodide salt can be sodium iodide (NaI) or potassium iodide (KI). In some embodiments, the coupling reaction mixture further includes an iodide salt selected from the group consisting of sodium iodide and potassium iodide. In some embodiments, the coupling reaction mixture further includes potassium iodide. In other embodiments, the coupling reaction mixture further includes sodium iodide.

The iodide salt can be present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some embodiments, potassium iodide is present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some other embodiments, potassium iodide is present in the coupling reaction mixture in an amount of 1.0 molar equivalent, relative to the compound of Formula (IV). In some embodiments, sodium iodide is present in the coupling reaction mixture in an amount of from 0.5 to 2 molar equivalents, 1 to 1.5 molar equivalents, 1 to 1.3 molar equivalents, 1 to 1.2 molar equivalents, or 1.0 molar equivalent, relative to the compound of Formula (IV). In some other embodiments, sodium iodide is present in the coupling reaction mixture in an amount of 1.0 molar equivalent, relative to the compound of Formula (IV).

In some embodiments, the coupling reaction mixture further includes an aprotic solvent. Example of aprotic solvents include, but are not limited to, N-methylpyrrolidone (NMP), tetrahydrofuran (THF), ethyl acetate (EtOAc), acetone, dimethylformamide (DMF), acetonitrile (MeCN), dimethyl sulfoxide (DMSO), and hexamethylphosphoramide (HMPA). In some embodiments, the aprotic solvent is dimethylformamide.

As described above, the base such as di-($C_1$-$C_4$ alkyl) amines or tri-($C_1$-$C_4$ alkyl)amines can be sometimes used as solvents. In those embodiments, the coupling reaction mixture does not include an additional aprotic solvent.

The coupling reaction can be carried out at a molar concentration of from 0.1 to 2 mol/L, 0.2 to 1.5 mol/L, 0.2 to 1.0 mol/L, 0.2 to 0.5 mol/L, or 0.3 to 0.5 mol/L, based on the compound of Formula (IV). In some embodiments, the molar concentration of the compound of Formula (IV) in the coupling reaction mixture reaction is from 0.1 to 2 mol/L, 0.2 to 1.5 mol/L, 0.2 to 1.0 mol/L, 0.2 to 0.5 mol/L, or 0.3 to 0.5 mol/L. In some embodiments, the molar concentration of the compound of Formula (IV) in the coupling reaction mixture reaction is from 0.2 to 1.0 mol/L, 0.2 to 0.5 mol/L, or 0.3 to 0.5 mol/L. In other embodiments, the molar concentration of the compound of Formula (IV) in the coupling reaction mixture reaction is from 0.3 to 0.5 mol/L.

In some embodiments, the compound of Formula III is a compound of Formula III-1:

(III-1)

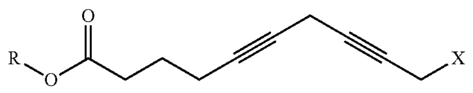

or a compound of Formmula III-2:

(III-2)

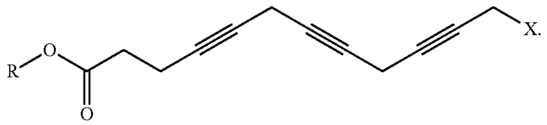

In some embodiments, the compound of Formula IV is a compound of Formula IV-1:

(IV-1)

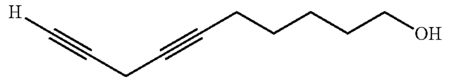

or a compound of Formula IV-2:

(IV-2)

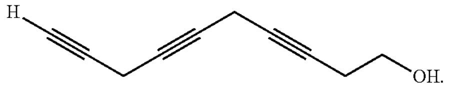

In some embodiments, the compound of Formula II is selected from the group consisting of:

(II-1)

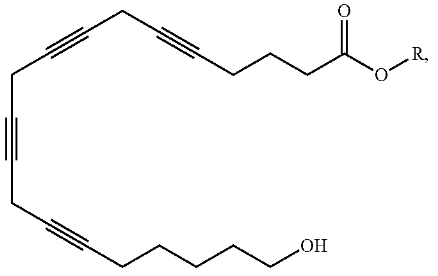

9II-2)

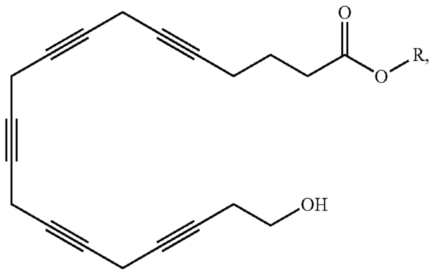

and (II-3)

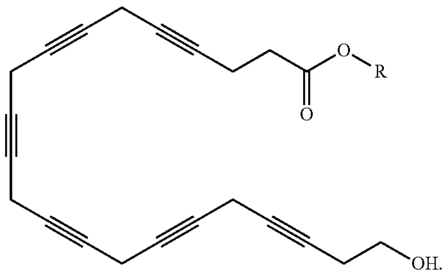

For example, non-limiting examples of $C_1$-$C_4$ alkyl include methyl, ethyl, isopropyl, and t-butyl. In some embodiments, R is methyl. In some embodiments, R is ethyl. In other embodiments, R is t-butyl.

In some embodiments, X is Cl, Br, I, or —OTs. In some embodiments, X is Cl. In other embodiments, X is Br. In other embodiments, X is I. In still other embodiments, X is —OTs.

In various embodiments, the method including:

forming a coupling reaction mixture comprising a transition-metal coupling agent, a base, a compound of Formula III-1:

(III-1)

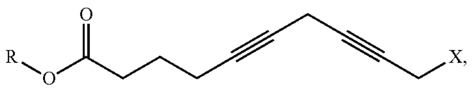

and a compound of Formula IV-1:

(IV-1)

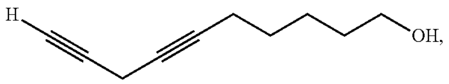

under conditions suitable to form a compound of Formula II-1:

(II-1)

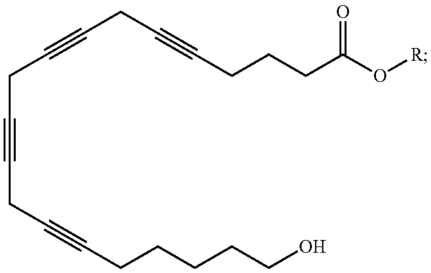

wherein the transition-metal coupling agent, the base, R, and X are as defined and described herein.

In various embodiments, the method including:

forming a coupling reaction mixture comprising a transition-metal coupling agent, a base, a compound of Formula III-1:

(III-1)

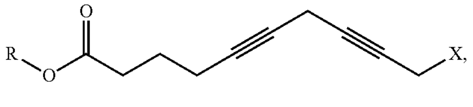

and a compound of Formula IV-2:

(IV-2)

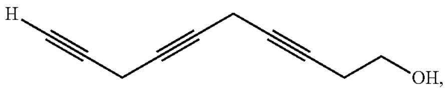

under conditions suitable to form a compound of Formula II-2:

(II-2)

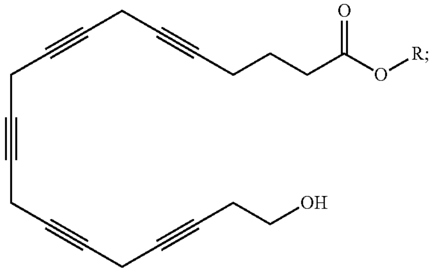

wherein the transition-metal coupling agent, the base, R, and X are as defined and described herein.

In various embodiments, the method including:

forming a coupling reaction mixture comprising a transition-metal coupling agent, a base, a compound of Formula III-2:

(III-2)

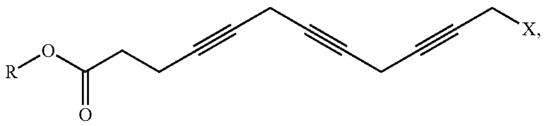

and a compound of Formula IV-2:

(IV-1)

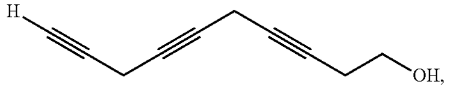

under conditions suitable to form a compound of Formula II-3:

(II-3)

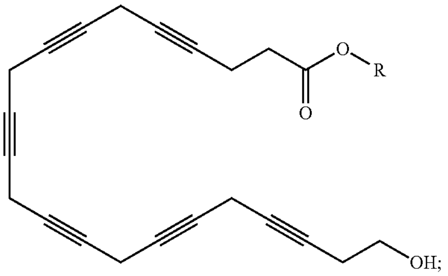

wherein the transition-metal coupling agent, the base, R, and X are as defined and described herein.

In some selected embodiments, the method including:

forming a coupling reaction mixture comprising a copper ion, an iodide salt, an alkali carbonate, an aprotic solvent, a compound of Formula III-1a:

(III-1a)

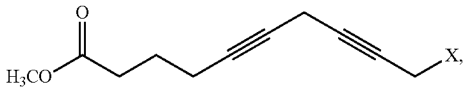

and a compound of Formula IV-1:

(IV-1)

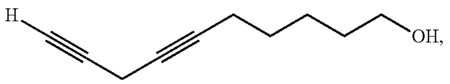

under conditions suitable to form a compound of Formula II-1:

(II-1a)

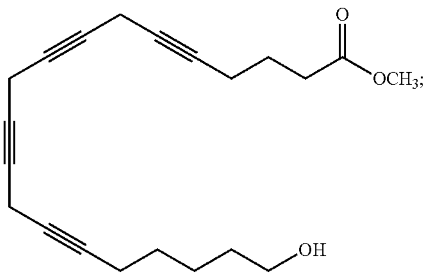

wherein the copper ion, the iodide salt, the alkali carbonate, the aprotic solvent, and X are as defined and described herein.

In some selected embodiments, the method including:

forming a coupling reaction mixture comprising a copper ion, an iodide salt, an alkali carbonate, an aprotic solvent, a compound of Formula III-1a:

(III-1a)

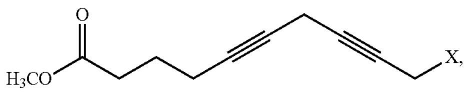

and a compound of Formula IV-2:

(IV-1)

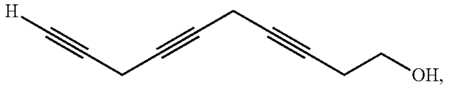

under conditions suitable to form a compound of Formula II-2a:

(II-2a)

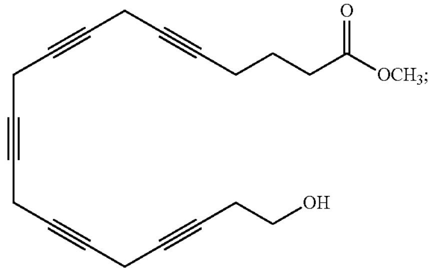

wherein the copper ion, the iodide salt, the alkali carbonate, the aprotic solvent, and X are as defined and described herein.

In some selected embodiments, the method including:

forming a coupling reaction mixture comprising a copper ion, an iodide salt, an alkali carbonate, an aprotic solvent, a compound of Formula III-2a:

(III-2a)

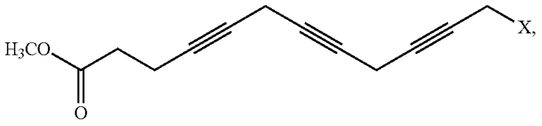

and a compound of Formula IV-2:

(IV-1)

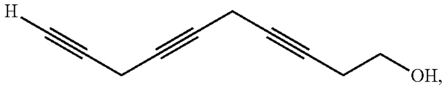

under conditions suitable to form a compound of Formula II-3a:

(II-3a)

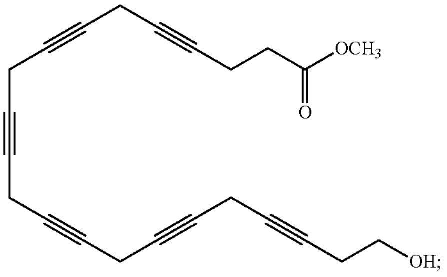

wherein the copper ion, the iodide salt, the alkali carbonate, the aprotic solvent, and X are as defined and described herein.

In one selected embodiment, the copper (I) ion salt is CuI.

In one selected embodiment, the iodide salt is sodium iodide.

In one selected embodiment, the alkali carbonate is cesium carbonate.

In one selected embodiment, the aprotic solvent is dimethylformamide.

In one selected embodiment, X is Br.

In general, the coupling reaction is carried out at room temperature. Elevated reaction temperature can be used to accelerate the reaction, especially on a large scale process. Initial cooling the reaction mixture may also be used on a large scale process. For example, the reaction temperature can be from 10° C. to 50° C., 20° C. to 40° C., 20° C. to 30° C., or about 25° C.

B. Alkenes of Formula I

In one aspect, provided herein is a method for preparing a compound of Formula I:

(I)

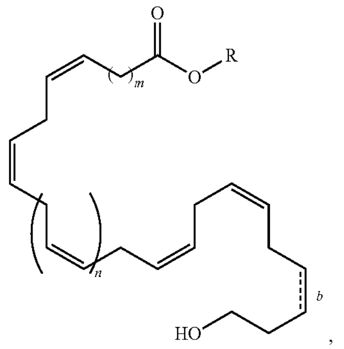

the method including:

i) forming a coupling reaction mixture comprising a transition-metal coupling agent, a base, a compound of Formula III:

(III)

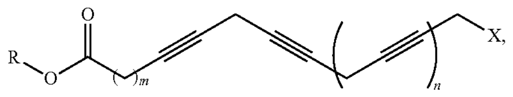

and a compound of Formula IV:

(IV)

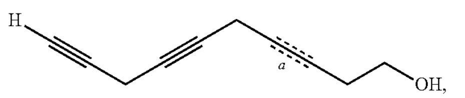

under conditions suitable to form a compound of Formula II:

(II)

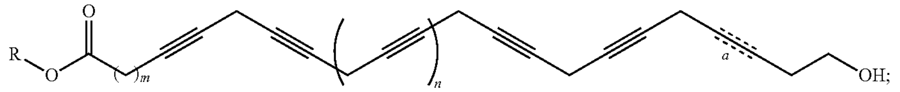

and ii) forming a hydrogenation reaction mixture comprising the compound of Formula II, a deactivated palladium catalyst, a deactivating agent, and hydrogen, under conditions suitable for hydrogenation to form the compound of Formula I;

wherein:

the transition-metal coupling agent comprises a metal selected from the group consisting of copper, iron, nickel, palladium, zinc, and combinations thereof;

R is $C_1$-$C_4$ alkyl;

X is selected from the group consisting of Cl, Br, I, —OTs, and —OTf;

subscript m is 2 or 3;

subscript n is 0 or 1; and bond a and bond b are each a single bond or bond a is a triple bond and bond b is a double bond.

R is as described in detail above. In one selected embodiments, R is methyl.

X is as described in detail above. In one selected embodiment, X is Br.

The transition-metal coupling agent is as described in detail above. In one selected embodiment, the transition metal coupling agent includes CuI.

The base is as described in detail above. In one selected embodiment, the base is cesium carbonate.

In some embodiments, the coupling reaction mixture further includes an iodide salt. The iodide salt is as described in detail above. In one selected embodiment, the iodide salt is sodium iodide.

In some embodiments, the coupling reaction mixture further includes an aprotic solvent. The aprotic solvent is as described in detail above. In one selected embodiment, the aprotic solvent is dimethylformamide.

The deactivated palladium catalysts can be prepared by poisoning a palladium catalyst with addition of various forms of lead and sulfur, N-containing heteroaryl compounds. Examples of "catalyst poisons" include, but are not limited to, the addition of lead acetate, lead oxide, quinolone, sulfides, thiols, or combinations thereof to the catalyst. Example of a commercial deactivated palladium catalyst is Lindlar catalyst. In some selected embodiments, the deactivated palladium catalyst is Lindlar catalyst.

In general, the deactivating agent is used to further poison the deactivated palladium catalyst in a reaction mixture. Further deactivating the deactivated palladium catalyst (e.g., Lindlar catalyst) is known to enhance the hydrogenation selectivity of alkynes to alkenes, preventing formation of alkanes. Examples of the deactivating agents include N-containing 5- to 10-membered heteroaryls, thiols, or diamines. Non-limiting examples of N-containing 5- to 10-membered heteroaryls include pyridine, picoline, lutidine, collidine, and quinolone. Non-limiting examples of thiols include 3,6-dithia-1,8-octanediol. Non-limiting examples of diamines include ethylenediamine. In some embodiments, the deactivating agent is selected from the group consisting of pyridine, quinoline, and ethylenediamine. In one selected embodiment, the deactivating agent includes pyridine. In another selected embodiment, the deactivating agent is pyridine.

In some embodiments of the hydrogenation, the hydrogenation reaction mixture further includes a $C_2$-$C_6$ alkene. Without being bond by theory, further addition of alkenes is found to improve the hydrogenation selectivity of alkynes (i.e., the compound of Formula II) to alkenes (i.e., the compound of Formula I), preventing formation of alkanes. In general, a branched $C_5$-$C_6$ non-terminal alkene is preferred. Non-limiting examples of branched non-terminal $C_5$-$C_6$ alkenes include 2-pentene, isopentene, 2-methyl-2-butene, 2-hexene, 2-methyl-2-pentene, 2,3-dimethyl-2-butene, (E)-3-methyl-2-pentene, (Z)-3-methyl-2-pentene, (E)-4-methyl-2-pentene, (Z)-4-methyl-2-pentene, and 3-hexene. In one selected embodiment, the $C_1$-$C_6$ alkene is 2-methyl-2-butene. In some selected embodiments of the hydrogenation, the hydrogenation reaction mixture further includes 2-methyl-2-butene.

Alkyne hydrogenation is known to be regioselective, occurring via syn addition to give the cis-alkene. Therefore, the hydrogenation of the compound of Formula II provides the compound of Formula I in all cis-configurations.

In various embodiments, the method including:

i) forming a coupling reaction mixture comprising a transition-metal coupling agent, a base, a compound of Formula III-1:

(III-1)

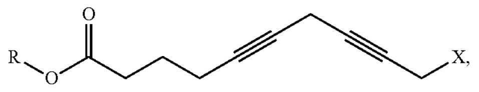

and a compound of Formula IV-1:

(IV-1)

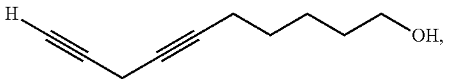

under conditions suitable to form a compound of Formula II-1:

(II-1)

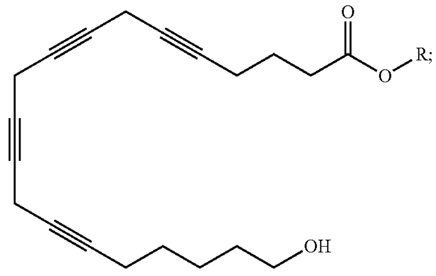

and ii) forming a hydrogenation reaction mixture comprising the compound of Formula II-1, a deactivated palladium catalyst, a deactivating agent, and hydrogen, under conditions suitable for hydrogenation to form the compound of Formula I-1:

(I-1)

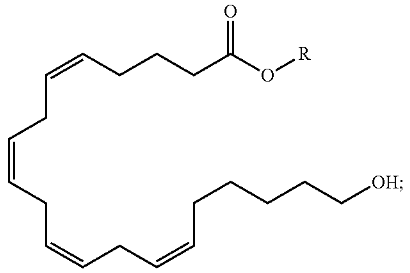

wherein the transition-metal coupling agent, the base, the deactivated palladium catalyst, the deactivating agent, R, and X are as defined and described herein.

In various embodiments, the method including:

i) forming a coupling reaction mixture comprising a transition-metal coupling agent, a base, a compound of Formula III-1:

(III-1)

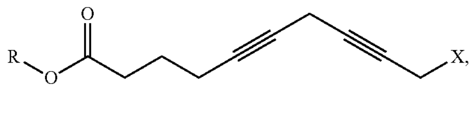

and a compound of Formula IV-2:

(IV-2)

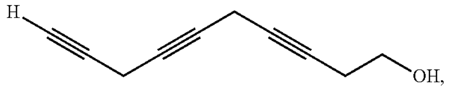

under conditions suitable to form a compound of Formula II-2:

(II-2)

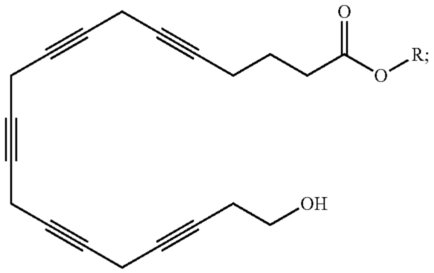

and ii) forming a hydrogenation reaction mixture comprising the compound of Formula II-2, a deactivated palladium catalyst, a deactivating agent, and hydrogen, under conditions suitable for hydrogenation to form the compound of Formula I-2:

(I-2)

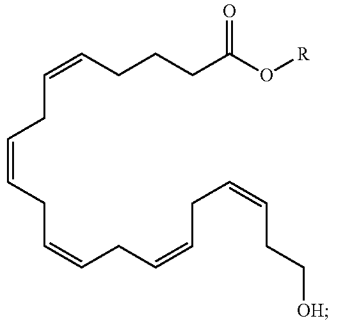

wherein the transition-metal coupling agent, the base, the deactivated palladium catalyst, the deactivating agent, R, and X are as defined and described herein.

In various embodiments, the method including:

i) forming a coupling reaction mixture comprising a transition-metal coupling agent, a base, a compound of Formula III-2:

(III-2)

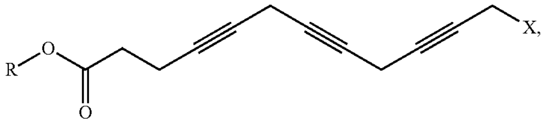

and a compound of Formula IV-2:

(IV-1)

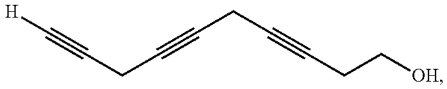

under conditions suitable to form a compound of Formula II-3:

(II-3)

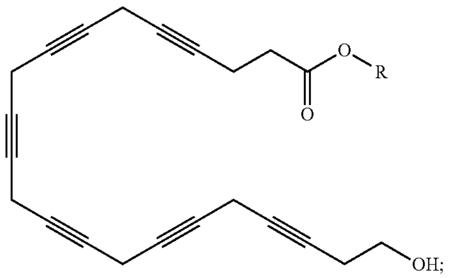

and ii) forming a hydrogenation reaction mixture comprising the compound of Formula II-3, a deactivated palladium catalyst, a deactivating agent, and hydrogen, under conditions suitable for hydrogenation to form the compound of Formula II-3:

(I-3)

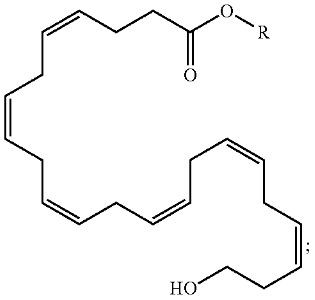

wherein the transition-metal coupling agent, the base, the deactivated palladium catalyst, the deactivating agent, R, and X are as defined and described herein.

In some selected embodiments, the method including:

i) forming a coupling reaction mixture comprising a copper ion, an iodide salt, an alkali carbonate, an aprotic solvent, a compound of Formula III-1a:

(III-1a)

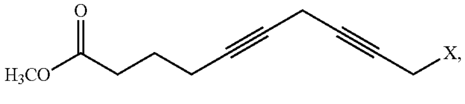

and a compound of Formula IV-1:

(IV-1)

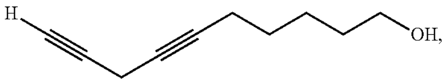

under conditions suitable to form a compound of Formula II-1a:

(II-1a)

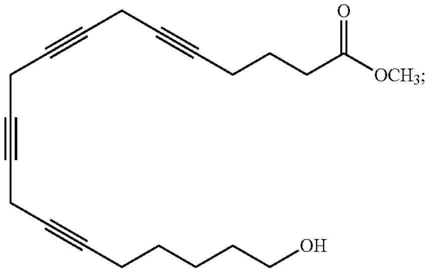

and ii) forming a hydrogenation reaction mixture comprising the compound of Formula II-1a, Lindlar catalyst, a N-containing 5- to 10-membered heteroaryl compound, a $C_2$-$C_6$ alkene, and hydrogen, under conditions suitable for hydrogenation to form the compound of Formula I-1a:

(I-1a)

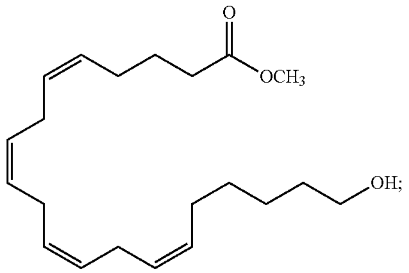

wherein the copper ion, the iodide salt, the alkali carbonate, the aprotic solvent, the N-containing 5- to 10-membered heteroaryl compound, the $C_2$-$C_6$ alkene, and X are as defined and described herein.

In some selected embodiments, the method including:

i) forming a coupling reaction mixture comprising a copper ion, an iodide salt, an alkali carbonate, an aprotic solvent, a compound of Formula III-1a:

(III-1a)

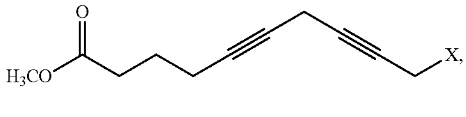

and a compound of Formula IV-2:

(IV-2)

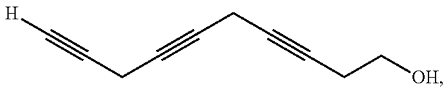

under conditions suitable to form a compound of Formula II-2a:

(II-2a)

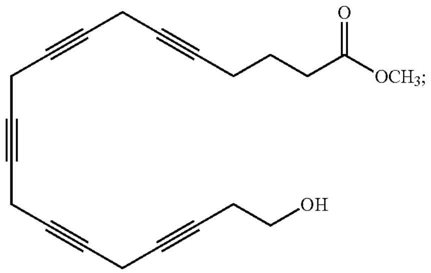

and ii) forming a hydrogenation reaction mixture comprising the compound of Formula II-2a, Lindlar catalyst, a N-containing 5- to 10-membered heteroaryl compound, a $C_2$-$C_6$ alkene, and hydrogen, under conditions suitable for hydrogenation to form the compound of Formula I-2a:

(I-2a)

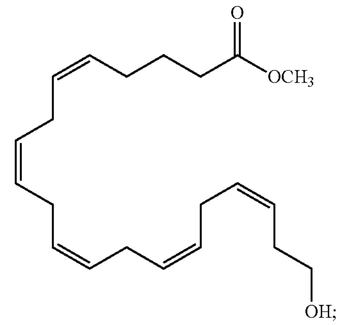

wherein the copper ion, the iodide salt, the alkali carbonate, the aprotic solvent, the N-containing 5- to 10-membered heteroaryls compound, the $C_2$-$C_6$ alkene, and X are as defined and described herein.

In some selected embodiments, the method including:

i) forming a coupling reaction mixture comprising a copper ion, an iodide salt, an alkali carbonate, an aprotic solvent, a compound of Formula III-2a:

(III-2a)

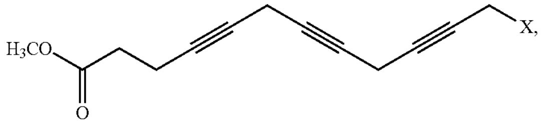

and a compound of Formula IV-2:

(IV-1)

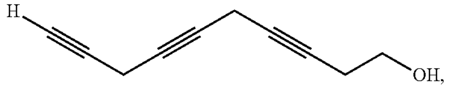

under conditions suitable to form a compound of Formula II-3a:

(II-3a)

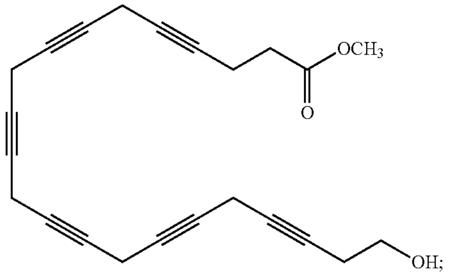

and ii) forming a hydrogenation reaction mixture comprising the compound of Formula II-3a, Lindlar catalyst, a N-containing 5- to 10-membered heteroaryl compound, a $C_2$-$C_6$ alkene, and hydrogen, under conditions suitable for hydrogenation to form the compound of Formula I-3a:

(I-3a)

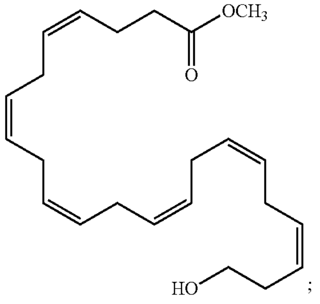

wherein the copper ion, the iodide salt, the alkali carbonate, the aprotic solvent, the N-containing 5- to 10-membered heteroaryl compound, the $C_2$-$C_6$ alkene, and X are as defined and described herein.

In one selected embodiment, X is Br.

In one selected embodiment, the copper ion includes CuI.

In one selected embodiment, the iodide salt is sodium iodide.

In one selected embodiment, the base is cesium carbonate.

In one selected embodiment, the aprotic solvent is dimethylformamide.

In one selected embodiment, the N-containing 5-10 heteroaryl compound is pyridine.

In one selected embodiment, the $C_2$-$C_6$ alkene is 2-methyl-2-butene.

In general, the hydrogenation reaction is carried out at room temperature under hydrogen atmosphere. Suitable solvents for the hydrogenation include, but are not limited to, an alcohol (e.g., methanol or ethanol) and ethyl acetate. The hydrogen pressure for the reaction can be, for example one atmosphere.

C. Omega-Hydroxylated Polyunsaturated Fatty Acids

In some embodiments of preparing the compound of Formula I, the method further includes the preparation of ω-hydroxylated polyunsaturated fatty acid having a structure of:

(20-HETE)

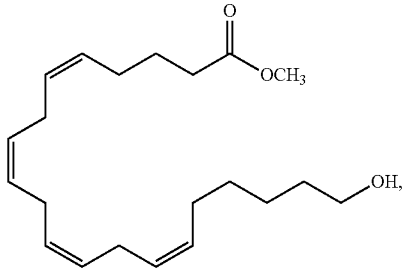

(20-HEPE)

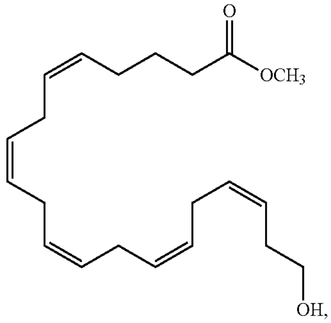

or

-continued (22-HDoHE)

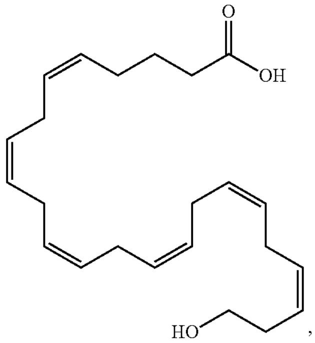

or a salt thereof, the method including:

forming a hydrolysis reaction mixture comprising an alkali hydroxide and the compound of Formula I-1, 1-2, or 1-3:

(I-1)

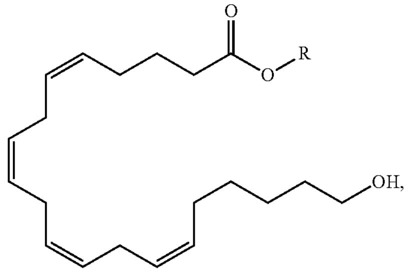

(I-2)

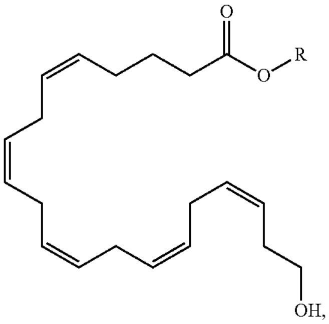

or (I-3)

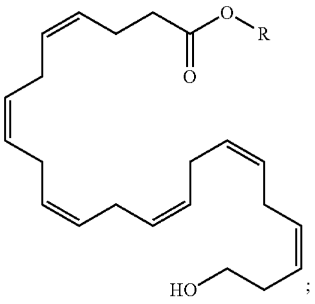

under conditions suitable for saponification to form the corresponding 20-HETE, 20-HEPE, or 22-HdoHE, or a salt thereof;

wherein R is methyl or ethyl.

Suitable alkali hydroxides include LiOH, NaOH, and KOH. In some embodiments, the alkali hydroxide is selected from the group consisting of LiOH, NaOH, and KOH. In one selected embodiment, the alkali hydroxide is LiOH. In another selected embodiment, the alkali hydroxide is NaOH.

Suitable solvents for saponification include, but are not limited to, water, an alcohol (e.g., methanol or ethanol), ether (e.g., THF), or a mixture thereof. In some embodiments, when R is methyl, the hydrolysis reaction mixture further includes methanol. In other embodiments, when R is ethyl, the hydrolysis reaction mixture further includes ethanol. In some other embodiments, the hydrolysis reaction mixture further includes a mixture of water and THF.

In general, the hydrolysis of the ester is carried out at room temperature.

In other embodiments of preparing the compound of Formula I wherein R is t-butyl, the method further includes forming a deprotection reaction mixture comprising the compound of Formula I-1, I-2, or I-3 and a strong acid under conditions suitable for deprotecting the t-butyl group to form the corresponding 20-HETE, 20-HEPE, or 22-HdoHE. Suitable strong acids include, but are not limited to, HCl, sulfuric acid, and trifloroacetic acid.

In one aspect, provided herein is a method of preparing a ω-hydroxylated polyunsaturated fatty acid having a structure of:

(20-HETE)

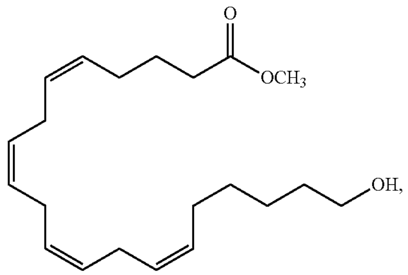

or (20-HEPE)

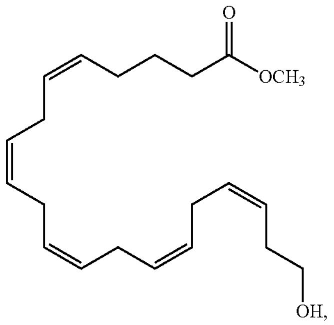

or a salt thereof, the method including:

i) forming a coupling reaction mixture comprising a copper ion, an iodide salt, an alkali carbonate, an aprotic solvent, a compound of Formula III-1a:

(III-1a)

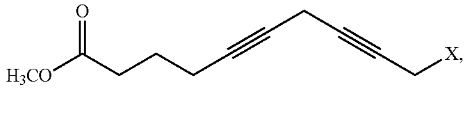

and a compound of Formula Iv-1 or Iv-2:

(IV-1)

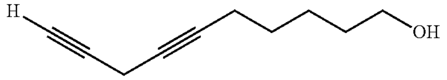

(IV-2)

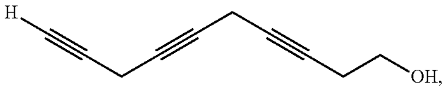

under conditions suitable to form a corresponding compound of Formula II-1a or II-2a:

(II-1a)

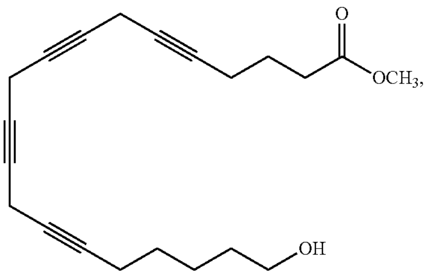

(II-2a)

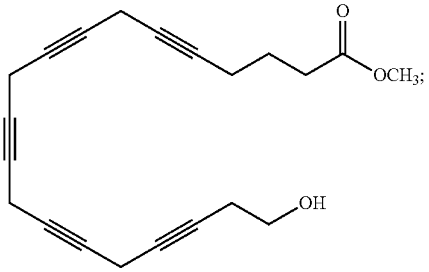

ii) forming a hydrogenation reaction mixture comprising the compound of Formula II-1a or II-2a, Lindlar catalyst, a N-containing 5- to 10-membered heteroaryl compound, a $C_2$-$C_6$ alkene, and hydrogen, under conditions suitable for hydrogenation to form a corresponding compound of Formula I-1a or I-2a:

(I-1a)

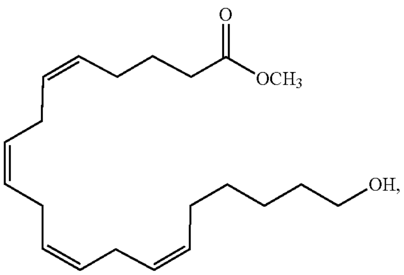

-continued (I-2a)

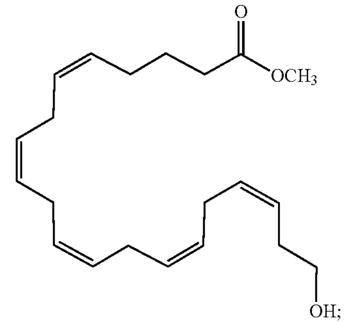

iii) forming a hydrolysis reaction mixture comprising the compound of Formula I-1a or I-2a and an alkali hydroxide under conditions suitable for saponification to form the corresponding 20-HETE or 20-HEPE;

wherein:

the copper ion is a copper (I) ion salt selected from the group consisting of CuI, CuBr, CuCl, and Cu(OAc); and X is selected from the group consisting of Cl, Br, I, and —OTs.

In another aspect, provided herein is a method of preparing a ω-hydroxylated polyunsaturated fatty acid having a structure of:

(22-HDoHE)

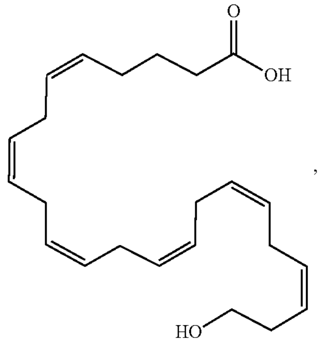

, or a salt thereof;

the method includes:

i) forming a coupling reaction mixture comprising a copper ion, an iodide salt, an alkali carbonate, an aprotic solvent, a compound of Formula III-2a:

(III-2a)

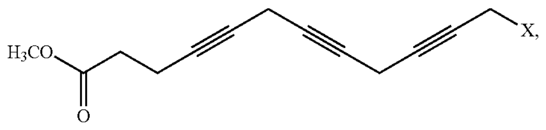

and a compound of Formula IV-2:

(IV-2)

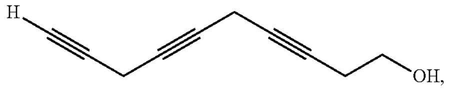

under conditions suitable to form the compound of Formula II-3a:

(II-3a)

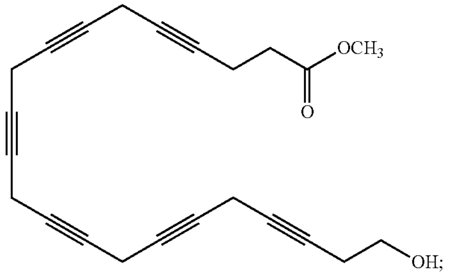

ii) forming a reaction mixture comprising a compound of Formula II-3a, Lindlar catalyst, a N-containing 5- to 10-membered heteroaryl compound, a $C_2$-$C_6$ alkene, and hydrogen, under conditions suitable for hydrogenation to form a compound of Formula I-3a:

(I-3a)

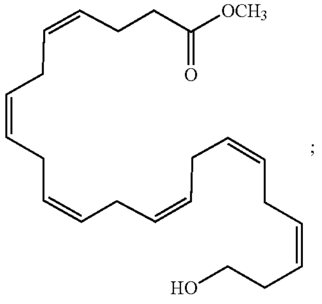

;

iii) forming a hydrolysis reaction mixture comprising the compound of Formula I-3a and an alkali hydroxide under conditions suitable for saponification to form 22-HdoHE;

wherein:

the copper ion is a copper (I) ion salt selected from the group consisting of CuI, CuBr, CuCl, and Cu(OAc); and X is selected from the group consisting of Cl, Br, I, and —OTs.

The iodide salt, the alkali carbonate, the aprotic solvent, the N-containing 5- to 10-membered heteroaryl compound, the $C_2$-$C_6$ alkene, and the alkali hydroxide are as defined and described herein.

In one selected embodiment, the copper (I) ion salt is CuI.

In one selected embodiments, the iodide salt is sodium iodide.

In one selected embodiment, the alkali carbonate is cesium carbonate.

In one selected embodiment, the aprotic solvent is dimethylformamide.

In one selected embodiment, the N-containing 5- to 10-membered heteroaryl compound is pyridine.

In one selected embodiment, the $C_2$-$C_6$ alkene is 2-methyl-2-butene.

In one selected embodiment, the alkali hydroxide is NaOH. In another selected embodiment, the alkali hydroxide is LiOH.

In some selected embodiments, the hydrolysis reaction mixture further includes methanol. In other selected embodiments, the hydrolysis reaction mixture further includes a mixture of water and THF.

In one selected embodiment, X is Br.

In one selected embodiment, the method including:

i) forming a coupling reaction mixture comprising CuI, NaI, $CsCO_3$, DMF, a compound of Formula III-1a-Br:

(III-1a-Br)

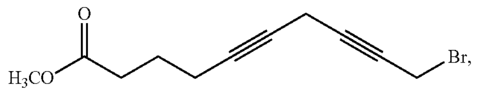

a compound of Formula Iv-1 or Iv-2:

(IV-1)

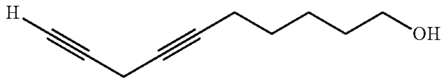

(IV-2)

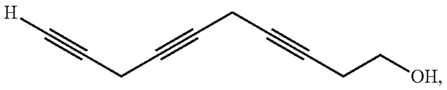

under conditions suitable to form a corresponding compound of Formula II-1a or II-2a:

(II-1a)

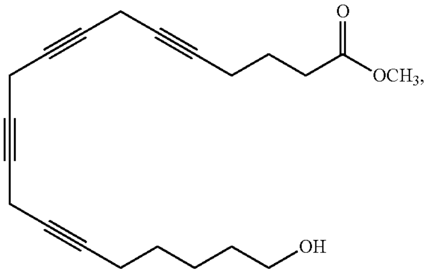

(II-2a)

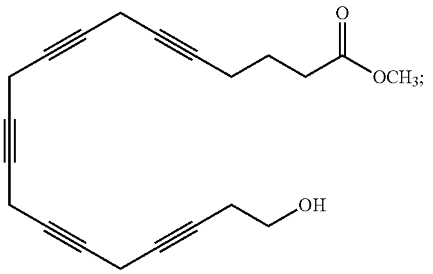

ii) forming a hydrogenation reaction mixture comprising the compound of Formula II-1a or II-2a, Lindlar catalyst, pyridine, 2-methyl-2-butene, a hydrogenation solvent, and hydrogen, under conditions suitable for hydrogenation to form a corresponding compound of Formula I-1a or I-2a:

(I-1a)

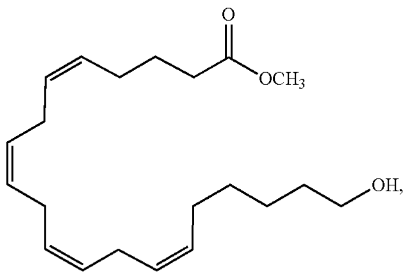

(I-2a)

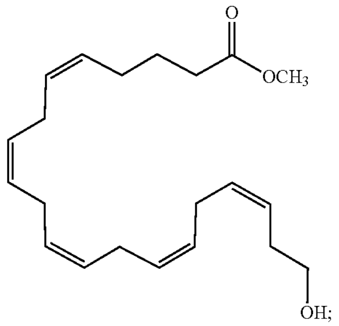

iii) forming a hydrolysis reaction mixture comprising the compound of Formula I-1a or I-2a, an alkali hydroxide, and a hydrolysis solvent under conditions suitable for saponification to form 20-HETE or 20-HEPE, or a salt thereof Wherein:

the hydrogenation solvent is methanol, ethanol or ethyl acetate;

the alkali hydroxide is NaOH or LiOH; and the hydrolysis solvent is methanol or a mixture of water and THF.

In another selected embodiment, the method including:

i) forming a coupling reaction mixture comprising CuI, NaI, $CsCO_3$, DMF, a compound of Formula III-2a-Br:

(III-2a-Br)

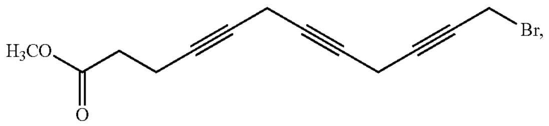

and a compound of Formula IV-2:

(IV-2)

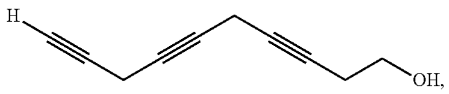

under conditions suitable to form the compound of Formula II-3a:

(II-3a)

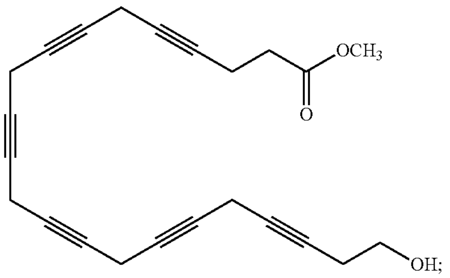

For the coupling reaction, other parameters (e.g., the molar equivalents of the copper ion, the iodide salt, the alkali carbonate; the concentration of the reaction; and reaction temperature) are as described in detail above.

For the hydrogenation reaction, other parameters (e.g., reaction temperature and hydrogen pressure) are as described in detail above.

For the hydrolysis reaction, the reaction temperature is as described above.

IV. Compounds

In one aspect, provided herein is a compound of Formula II:

(II)

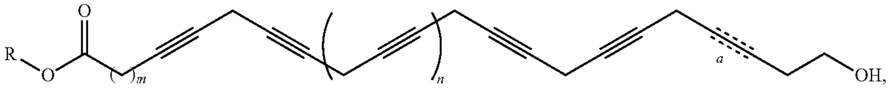

ii) forming a reaction mixture comprising a compound of Formula II-3a, Lindlar catalyst, pyridine, 2-methyl-2-butene, a hydrogenation solvent; and hydrogen, under conditions suitable for hydrogenation to form a compound of Formula I-3a:

(I-3a)

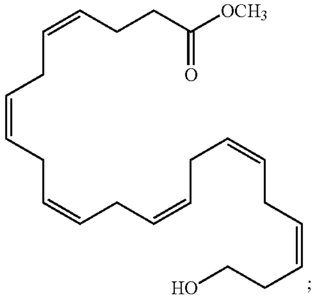

iii) forming a hydrolysis reaction mixture comprising the compound of Formula I-3a, an alkali hydroxide, and a hydrolysis solvent under conditions suitable for saponification to form 22-HdoHE or a salt thereof;

Wherein:

the hydrogenation solvent is methanol, ethanol or ethyl acetate;

the alkali hydroxide is NaOH or LiOH; and the hydrolysis solvent is methanol or a mixture of water and THF.

In one selected embodiment, the hydrogenation solvent is methanol. In one selected embodiment, the hydrogenation solvent is ethanol. In another selected embodiment, the hydrogenation solvent is ethyl acetate.

In one selected embodiment, the alkali hydroxide is NaOH. In another selected embodiment, the alkali hydroxide is LiOH.

In one selected embodiment, hydrolysis solvent is methanol. In another selected embodiment, hydrolysis solvent is a mixture of water and THF.

wherein:

R is $C_1$-$C_4$ alkyl;

subscript m is 2 or 3;

subscript n is 0 or 1; and bond a is a single bond or a triple bond.

In various embodiments, the compound of Formula II is a compound of Formula II-1:

(II-1)

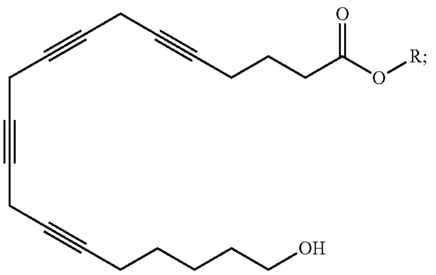

wherein R is as defined herein.

In various embodiments, the compound of Formula II is a compound of Formula II-2:

(II-2)

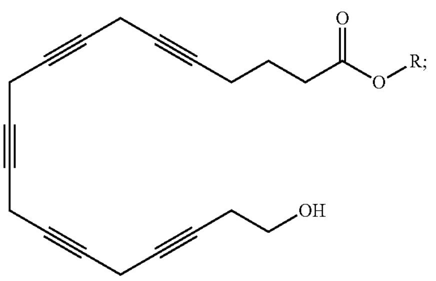

wherein R is as defined herein.

In various embodiments, the compound of Formula II is a compound of Formula II-3:

(II-3)

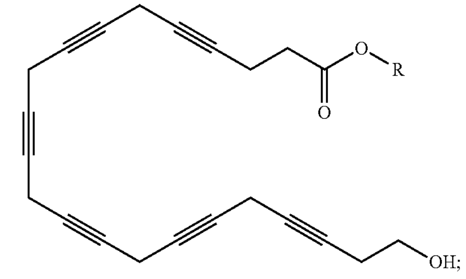

wherein R is as defined herein.

In some embodiments, R is methyl. In some embodiments, R is ethyl. In other embodiments, R is isopropyl. In other embodiments, R is t-butyl.

In one selected embodiment, the compound of Formula II is a compound of Formula II-1a, II-2a, or II-3a:

(II-1)

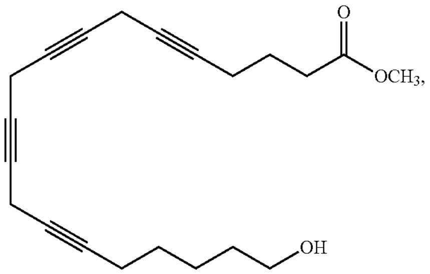

(II-2)

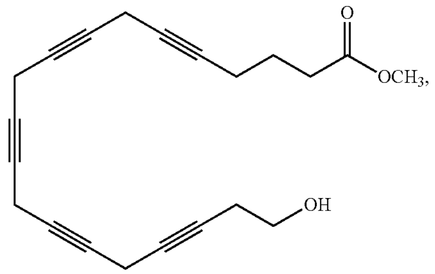

or (II-3)

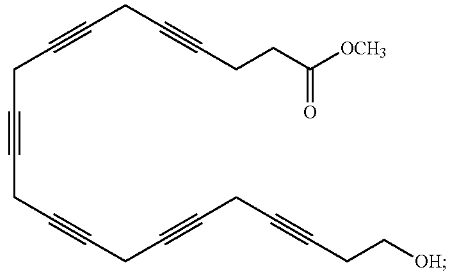

V. Pharmaceutical Compositions

In one aspect, provided herein is a pharmaceutical composition including a ω-hydroxylated polyunsaturated fatty acid, or an ester form thereof, and a pharmaceutically acceptable excipient.

In some embodiments of the pharmaceutical compositions, the ω-hydroxylated polyunsaturated fatty acid, or an ester form thereof, is included in a therapeutically effective amount.

In some embodiments, the ω-hydroxylated polyunsaturated fatty acid is selected from the group consisting of 20-HETE, 20-HEPE, and 22-HDoHE, and mixtures thereof. In some embodiments, the ω-hydroxylated polyunsaturated fatty acid is 20-HETE. In some embodiments, the ω-hydroxylated polyunsaturated fatty acid is 20-HEPE. In other embodiments, the ω-hydroxylated polyunsaturated fatty acid is 22-HDoHE.

In some other embodiments, the ester form of the ω-hydroxylated polyunsaturated fatty acid is a compound of formula I. In some embodiments, the ester form of the ω-hydroxylated polyunsaturated fatty acid is methyl ester. In some embodiments, the methyl ester form of the ω-hydroxylated polyunsaturated fatty acid is a compound selected from the group consisting of Formula I-1a, I-2a, and I-3a. In some embodiments, the methyl ester form of the ω-hydroxylated polyunsaturated fatty acid is a compound of Formula I-1a. In some embodiments, the methyl ester form of the ω-hydroxylated polyunsaturated fatty acid is a compound of Formula I-2a. In some embodiments, the methyl ester form of the ω-hydroxylated polyunsaturated fatty acid is a compound of Formula I-3a.

In some embodiments of the pharmaceutical compositions, the pharmaceutical composition includes a second agent (e.g. therapeutic agent). In some embodiments of the pharmaceutical compositions, the pharmaceutical composition includes a second agent (e.g. therapeutic agent) in a therapeutically effective amount. In some embodiments of the pharmaceutical compositions, the second agent is an agent for treating cancer. In some embodiments, the second agent is an anti-cancer agent. In other embodiments, the second agent is a chemotherapeutic.

VI. Methods of Use

In one aspect, provided herein is a method of treating cancer or macular degeneration, the method including administering to a subject in need thereof an effective amount of a ω-hydroxylated polyunsaturated fatty acid, or the ester form thereof, or a pharmaceutical composition thereof. In some embodiments, the ω-hydroxylated polyunsaturated fatty acid, or an ester form thereof, is included in a therapeutically effective amount.

In some aspects, the method of treating cancer includes administering to a subject in need thereof an effective amount of a ω-hydroxylated polyunsaturated fatty acid, or the ester form thereof, or a pharmaceutical composition thereof. In some embodiments, the cancer is colorectal cancer. In some embodiments, the cancer is liver cancer. In some embodiments, the cancer is hepatocellular cancer. In other embodiments, the cancer is breast cancer. In other embodiments, the cancer is renal adenocarcinoma.

In some embodiments, the cancer is estrogen receptor positive breast cancer. In other embodiments, the cancer is estrogen receptor (ER) negative breast cancer. In some embodiments, the cancer is tamoxifen resistant breast cancer. In some embodiments, the cancer is HER2 negative breast cancer. In other embodiments, the cancer is HER2 positive breast cancer. In some embodiments, the cancer is low grade (well differentiated) breast cancer. In other embodiments, the cancer is intermediate grade (moderately differentiated) breast cancer. In still other embodiments, the cancer is high grade (poorly differentiated) breast cancer. In some embodiments, the cancer is stage 0 breast cancer. In some embodiments, the cancer is stage I breast cancer. In some embodiments, the cancer is stage II breast cancer. In other embodiments, the cancer is stage III breast cancer. In other embodiments, the cancer is stage IV breast cancer. In still other embodiments, the cancer is triple negative breast cancer.

In other aspects, the method of treating macular degeneration includes administering to a subject in need thereof an effective amount of a ω-hydroxylated polyunsaturated fatty acid, or the ester form thereof, or a pharmaceutical composition thereof. In some embodiments, the ω-hydroxylated polyunsaturated fatty acid, or an ester form thereof, is included in a therapeutically effective amount.

In some embodiments, the ω-hydroxylated polyunsaturated fatty acid inhibits tumor growth, angiogenesis, lymphangiogenesis, or combinations thereof.

Angiogenesis is the physiological process through which new blood vessels form from pre-existing vessels. Angiogenesis is a normal and vital process in growth and development, as well as in wound healing and in the formation of granulation tissue. However, it is also a fundamental step in the transition of tumors from a benign state to a malignant one, leading to the use of angiogenesis inhibitors in the treatment of cancer. Vascular endothelial growth factor (VEGF) has been demonstrated to be a major contributor to angiogenesis, increasing the number of capillaries in a given network. In some embodiments, the ω-hydroxylated polyunsaturated fatty acid inhibits VEGF-induced angiogenesis. In some embodiments, the ω-hydroxylated polyunsaturated fatty acid inhibits tumor growth induced by VEGF.

Angiogenesis is defined as a new blood vessel sprouting from pre-existing vessels. This can be accomplished through endothelial sprouting or non-sprouting (intussusceptive) microvascular growth (IMG) The sprouting angiogenesis in tumor growth was reported to have the following stages: 1) The basement membrane is locally degraded on the side of the dilated peritumoral postcapillary venule situated closed to the angiogenic stimulus; 2) Interendothelial contacts are weakened and endothelial cells migrate into the connective tissue; 3) A solid cord of endothelial cells form; 4) Lumen formation occurs proximal to the migrating front, contiguous tubular sprouts anastomose to form functionally capillary loops, parallel with the synthesis of the new basement membrane and the recruitment of pericytes. In some embodiments, the ω-hydroxylated polyunsaturated fatty acid inhibits VEGF-induced endothelial cell migration. In particular, the ω-hydroxylated polyunsaturated fatty acid inhibits VEGF-induced endothelial cell migration in human umbilical vein endothelial cells (HUVECs).

Angiogenesis has been well established to play an essential role in cancer, through providing nutrients and oxygen to the tumors tissues to promote tumor progression. In some embodiments, the ω-hydroxylated polyunsaturated fatty acid inhibits tumor growth. In particular, the ω-hydroxylated polyunsaturated fatty acid inhibits tumor growth induced by VEGF.

Lymphangiogenesis is the formation of lymphatic vessels from pre-existing lymphatic vessels in a method believed to be similar to angiogenesis (blood vessel development). Lymphangiogenesis has been shown to play a critical role in tumor metastasis and many other human diseases. Tumor-induced lymphangiogenesis is mediated by lymphangiogenic growth factors that are produced and secreted by the tumors themselves, stromal cells, tumor-infiltrating macrophages, or activated platelets. In recent years, experimentation has focused on the role of VEGF-C and VEGF-D in cancer progression. The overexpression of either vascular endothelial growth factor-C (VEGF-C) or VEGF-D in tumors significantly increased tumor-associated lymphatic vessel growth (primarily at the tumor margin) and increased incidence of lymph node metastasis. In some embodiments, the ω-hydroxylated polyunsaturated fatty acid inhibits lymphangiogenesis. In particular, the ω-hydroxylated polyunsaturated fatty acid inhibits the vascular endothelial growth factor-C (VEGF-C)-induced tube formation in human dermal lymphatic endothelial cells (HMVEC-dLy).

In some embodiments, the ω-hydroxylated polyunsaturated fatty acid is selected from the group consisting of 20-HETE, 20-HEPE, and 22-HDoHE, and mixtures thereof. In some embodiments, the ω-hydroxylated polyunsaturated fatty acid is 20-HETE. In some embodiments, the ω-hydroxylated polyunsaturated fatty acid is 20-HEPE. In other embodiments, the ω-hydroxylated polyunsaturated fatty acid is 22-HDoHE.

In some other embodiments, the ester form of the ω-hydroxylated polyunsaturated fatty acid is a compound of formula I. In some embodiments, the ester form of the ω-hydroxylated polyunsaturated fatty acid is methyl ester. In some embodiments, the methyl ester form of the ω-hydroxylated polyunsaturated fatty acid is a compound selected from the group consisting of Formula I-1a, I-2a, and I-3a. In some embodiments, the methyl ester form of the ω-hydroxylated polyunsaturated fatty acid is a compound of Formula I-1a. In some embodiments, the methyl ester form of the ω-hydroxylated polyunsaturated fatty acid is a compound of Formula I-2a. In some embodiments, the methyl ester form of the ω-hydroxylated polyunsaturated fatty acid is a compound of Formula I-3a.

In some embodiments, the method includes administering a second agent (e.g. therapeutic agent). In some embodiments, the method includes administering a second agent (e.g. therapeutic agent) in a therapeutically effective amount. In some embodiments, the second agent is an agent for treating cancer. In other embodiments, the second agent is an anti-cancer agent. In other embodiments, the second agent is a chemotherapeutic.

VII. Examples

Example 1: General Chemical Methods

Example 1.1: Chemicals and Reagents

20-HETE used as a standard was purchased from Cayman Chemical (Ann Arbor, Mich.). All other reagents and solvents were obtained from commercial suppliers and were used without further purification. All reactions, unless otherwise described, were performed under an inert atmosphere of dry nitrogen.

Example 1.2: Instrumentation and Sample Analysis

Melting points were determined on an OptiMelt melting point apparatus and were uncorrected. $^{1}H$ NMR and $^{13}C$ NMR spectra were recorded at 300 and 75 MHz, respectively. Elemental analyses were determined at Midwest Microlab, Indianapolis, Ind. Mass. spectra were measured by LC-MS equipped with a Waters 2790 and a Waters PDA 996 using electrospray (+) ionization. Flash chromatography was performed on silica gel.

Example 1.3: Synthesis Schemes for Preparing ω-Hydroxylated Polyunsaturated Fatty Acids The syntheses of preparing ω-hydroxylated polyunsaturated fatty acids (i.e., 20-HETE, 20HEPE, and 22-HdoHE) are illustrated in Schemes 1 to 3.

Scheme 1
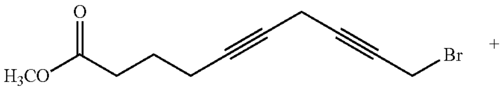
Formula III-1a-Br
Compound 3
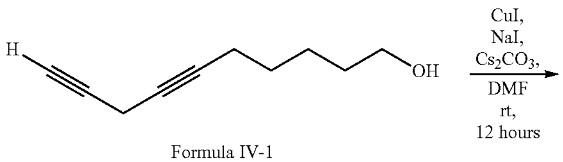
Formula IV-1
Compound 6
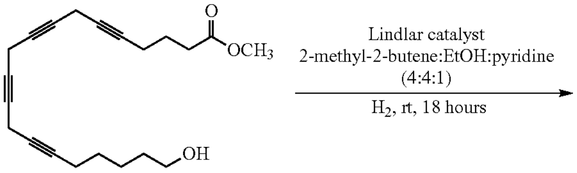
Formula II-1a
Compound 17
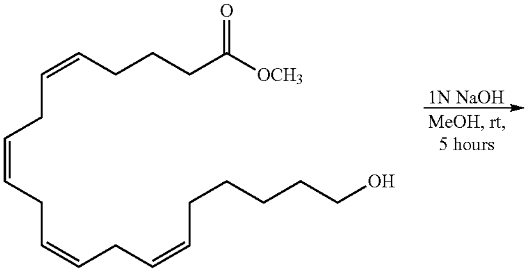
Formula I-1a
Compound 18
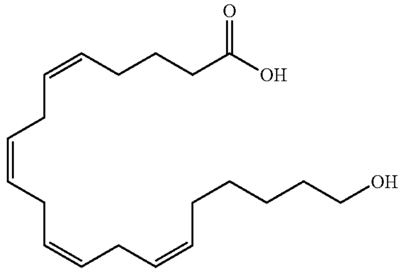
20-HETE
Scheme 2
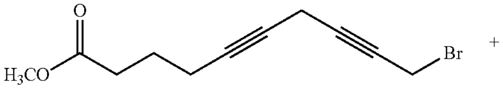
Formula III-1a-Br
Compound 3
-continued
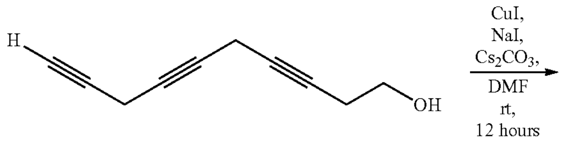
Formula IV-II
Compound 11
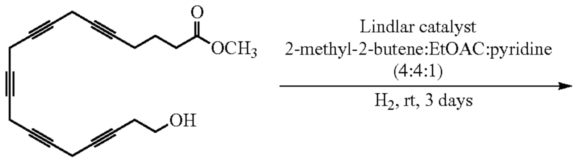
Formula II-2a
Compound 19
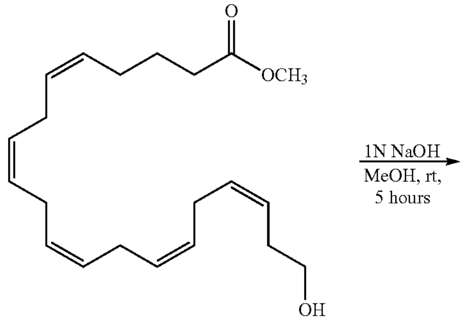
Formula I-2a
Compound 20
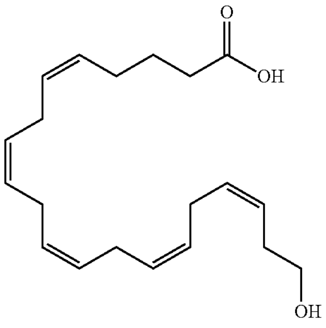
20-HEPE Scheme 3

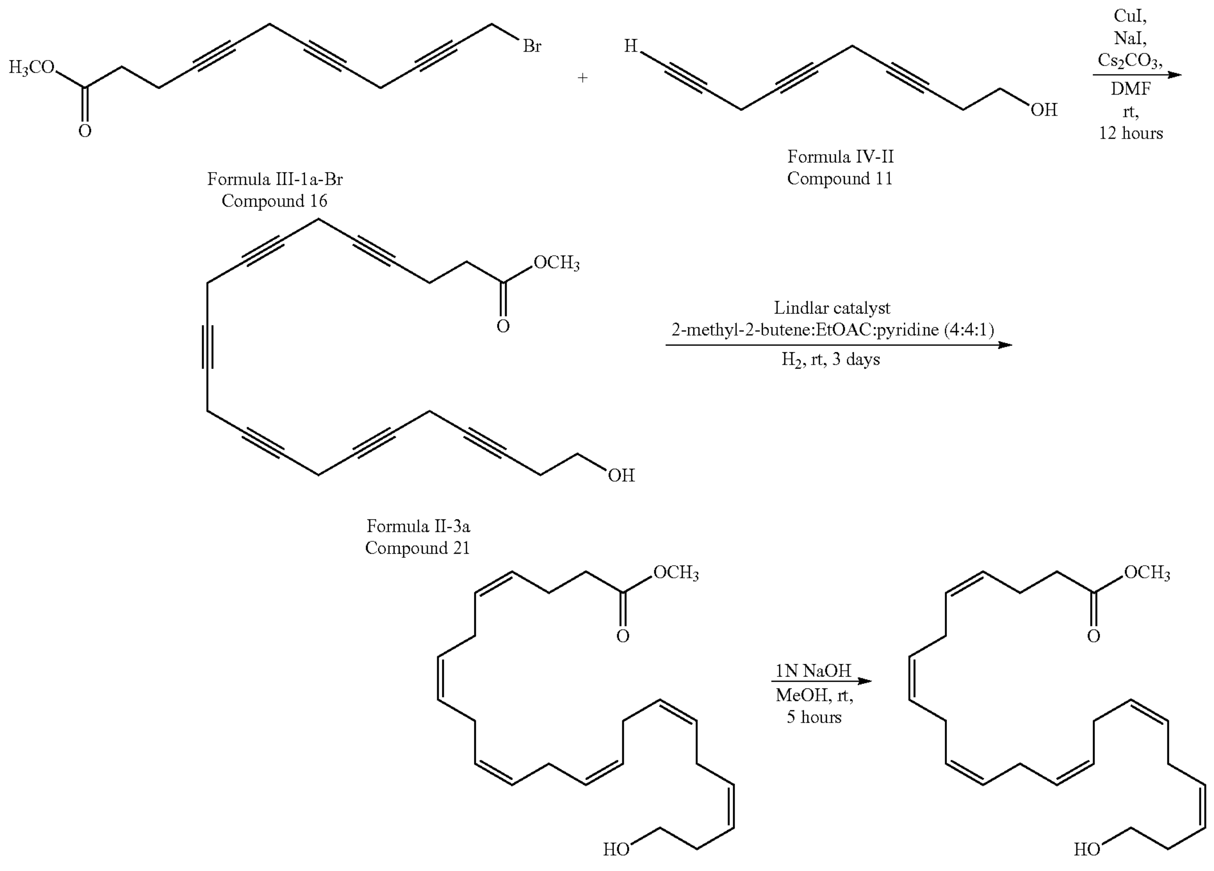

Formula III-1a-Br
Compound 16

+

Formula IV-II
Compound 11

Formula II-3a
Compound 21

Formula I-3a
Compound 22

22-HDoHE

Example 1.4: Synthesis Schemes for Preparing Intermediates

The compound of Formula III-1 can be prepared by a series of a copper (I)-mediated coupling reaction as described above and a conversion of the terminal —OH to Br (or Cl, I, —OTs, and —OTf). Accordingly, the preparation of the compound of Formula III-1a-Br is described in Scheme 4; and the preparation of the compound of Formula III-2a-Br is described in Scheme 5.

Scheme 4

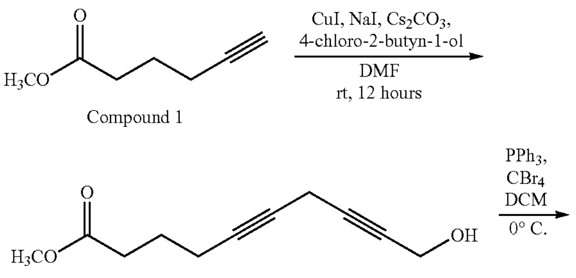

Compound 1

Compound 2

-continued

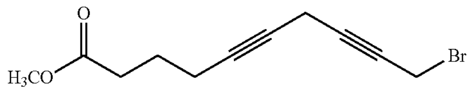

Formula III-1a-Br
Compound 3

Scheme 5

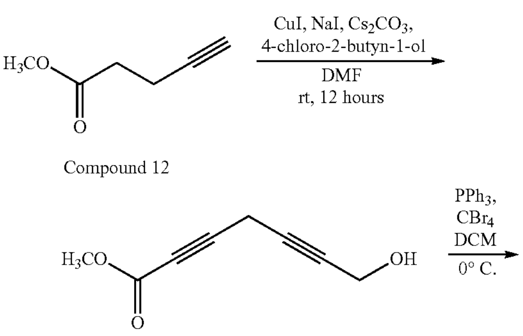

Compound 12

Compound 13

-continued

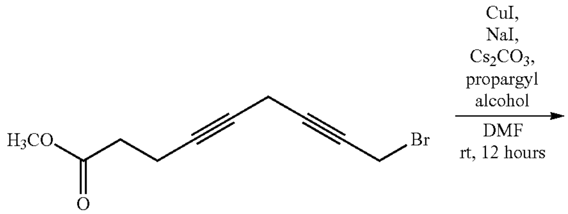

Compound 14

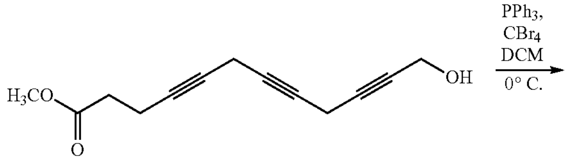

Compound 15

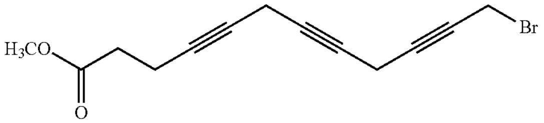

Formula III-1a-Br
Compound 16

The compound of Formula IV-1 or IV-2 can be prepared by a series of a copper (I)-mediated coupling reaction as described above and the removal of the silyl group. Accordingly, the preparation of the compound of Formula IV-1 is described in Scheme 6; and the preparation of the compound of Formula IV-2 is described in Scheme 7.

Scheme 6

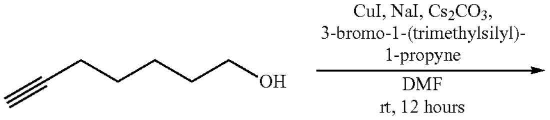

Compound 4

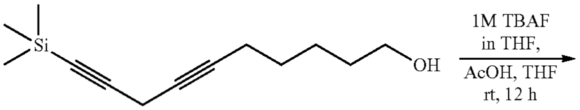

Compound 5

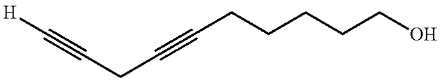

Formula IV-1
Compound 6

Scheme 7

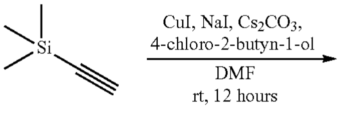

Compound 7

-continued

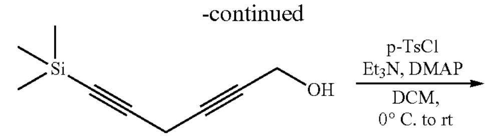

Compound 8

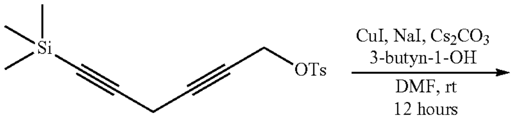

Compound 9

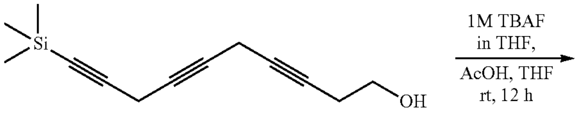

Compound 10

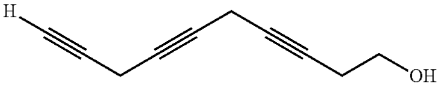

Formula IV-II
Compound 11

Example 2: Preparation of (5Z,8Z,11Z,14Z)-20-Hydroxyicosa-5,8,11,14-tetraenoic Acid (20-HETE)

Example 2.1: Synthesis of Methyl hex-5-ynoate (1)

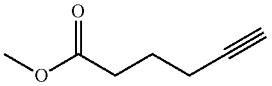

To a solution of 5-hexynoic acid (5 g, 44.6 mmol) in MeOH (400 mL) was added 10 drops of concentrated $H_2SO_4$ at room temperature. The reaction mixture was stirred for 2 days. The reaction mixture was quenched by adding 1 g of $K_2CO_3$ at room temperature. After 30 minutes, the solution was filtered and the filtrate was concentrated in vacuo. The remained residue was chromatographed on silica-gel to give the titled compound (3.94 g, 70%) as a colorless liquid. $^1$H NMR (400 MHz, $CDCl_3$): δ 3.67 (s, 3H), 2.45 (t, J=7 Hz, 2H), 2.26 (dt, J=7 and 3 Hz, 2H), 1.96 (t, J=3 Hz, 1H), 1.84 (p, J=7 Hz, 2H).

Example 2.2: Synthesis of Methyl 10-hydroxydeca-5,8-diynoate (2)

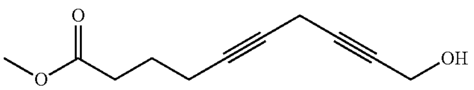

To a solution of methyl hex-5-ynoate (1) (4.4 g, 35 mmol) in DMF (50 mL) were added CuI (6.6 g, 35 mmol), NaI (5.2 g, 35 mmol), $Cs_2CO_3$ (11.4 g, 35 mmol), and 4-chlorobutyn-1-ol (3 mL, 35 mmol) at room temperature. The reaction mixture was stirred overnight. The reaction was quenched by adding saturated $NH_4Cl$ and extracted with $Et_2O$ (3×50 mL). The combined organic layers were washed with saturated $NH_4C_1$, aq. $Na_2S_2O_3$, and water, successively. After filtering, the solvents were removed in vacuo and the residue was purified by column chromatography to give the titled compound (4.2 g, 82%) as a clear oil. $^1$H NMR (400 MHz, $CDCl_3$): δ 4.23 (t, J=2 Hz, 2H), 3.66 (s, 3H), 3.16 (p, J=2 Hz, 2H), 2.42 (t, J=7 Hz, 2H), 2.22 (tt, J=7 and 2 Hz, 2H), 1.83 (s, 1H), 1.80 (p, J=7 Hz, 2H).

Example 2.3: Synthesis of Methyl 10-bromodeca-5,8-diynoate (3)

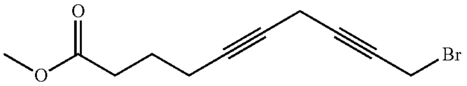

To a solution of methyl 10-hydroxydeca-5,8-diynoate (2) (2.55 g, 13.1 mmol) and tetrabromomethane (5.6 g, 16.9 mmol) in 130 mL of dichloromethane was added triphenylphosphine (4.6 g, 17.5 mmol) at 0° C. After stirring for 2 hours, the solvent was removed in vacuo. To the residue was added hexanes and the precipitates were removed by filter. The filtrate was concentrated in vacuo and purified by column chromatography to give the titled compound as a colorless oil (2.1 g, 81% yield). $^1$H NMR (400 MHz, $CDCl_3$): δ 3.90 (t, J=2 Hz, 2H), 3.67 (s, 3H), 3.20 (p, J=2 Hz, 2H), 2.42 (t, J=7 Hz, 2H), 2.23 (tt, J=7 and 2 Hz, 2H), 1.81 (p, J=7 Hz, 2H).

Example 2.4: Synthesis of 10-(Trimethylsilyl)deca-6,9-diyn-1-ol (5)

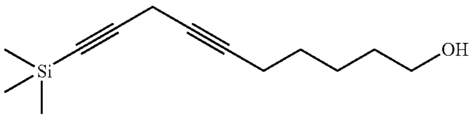

To a solution of 6-heptyn-1-ol (1.2 g, 10.5 mmol) in DMF (15 mL) were added CuI (2.0 g, 10.5 mmol), NaI (1.6 g, 10.5 mmol), $Cs_2CO_3$ (3.4 g, 10.5 mmol), and ethynyltrimethylsilane (2 g, 10.5 mmol) at room temperature. The reaction mixture was stirred overnight. The reaction was quenched by adding saturated $NH_4Cl$ and extracted with $Et_2O$ (3×50 mL). The combined organic layers were washed with saturated $NH_4Cl$, aq. $Na_2S_2O_3$, and water, successively. After filtering, the solvents were removed in vacuo and the residue was purified by column chromatography to give the titled compound (1.6 g, 69%) as a colorless oil. $^1$H NMR (400 MHz, $CDCl_3$): δ 3.63 (t, J=7 Hz, 2H), 3.17 (t, J=2 Hz, 2H), 2.17-2.10 (m, 2H), 1.71 (s, 1H), 1.58-1.37 (m, 6H), 0.14 (s, 9H).

Example 2.5: The Synthesis of Deca-6,9-diyn-1-ol (6)

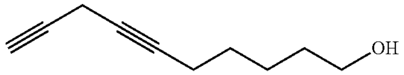

To a solution of 10-(trimethylsilyl)deca-6,9-diyn-1-ol (5) (1.1 g, 4.8 mmol) in 40 mL of THF were added tetrabutylammoniumfloride (1M in THF, 4.8 mL) and acetic acid (0.16 mL) simultaneously dropwise at room temperature. After stirring 1 h, the reaction mixture was extracted with $Et_2O$ (2 times). The combined organic layers were washed with water and brine. After drying with $MgSO_4$, the solvents were removed in vacuo. The remained residue was purified by column chromatography to give the titled compound (0.13 g, 81% yield) as a clear oil. $^1$H NMR (400 MHz, $CDCl_3$): δ 3.64 (t, J=7 Hz, 2H), 3.15-3.13 (m, 2H), 2.20-2.15 (m, 2H), 2.39 (s, 1H), 2.06 (t, J=3 Hz, 1H), 1.61-1.39 (m, 6H).

Example 2.6: Synthesis of Methyl 20-hydroxyicosa-5,8,11,14-tetraynoate (17)

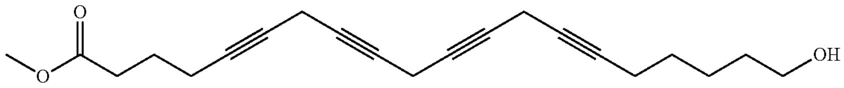 [SMILES: COC(=O)CCCC#CCC#CCC#CCC#CCCCCCO]

To a solution of deca-6,9-diyn-1-ol (6) (0.5 g, 3.3 mmol) in DMF (10 mL) were CuI (0.63 g, 3.3 mmol), NaI (0.49 g, 3.3 mmol), $Cs_2CO_3$ (1.1 g, 3.3 mmol), and methyl 10-bromodeca-5,8-diynoate (3) (0.93 g, 3.6 mmol) at room temperature. The reaction mixture was stirred overnight. The reaction was quenched by adding saturated $NH_4Cl$ and extracted with $Et_2O$ (3×20 mL). The combined organic layers were washed with saturated $NH_4C_1$, aq. $Na_2S_2O_3$, and water, successively. After filtering, the solvents were removed in vacuo and the residue was purified by column chromatography to give the titled compound (0.43 g, 40%) as a clear oil. $^1$H NMR (400 MHz, $CDCl_3$): δ 3.68 (s, 3H), 3.65 (t, J=7 Hz, 2H), 3.17-3.11 (m, 6H), 2.43 (t, J=7 Hz, 2H), 2.26-2.15 (m, 4H), 1.84-1.76 (m, 2H), 1.61-1.41 (m, 6H), 1.24 (s, 1H). MS (ESI) m/z: 335.59 ($M+H^+$).

Example 2.7: Synthesis of Methyl (5Z,8Z,11Z,14Z)-20-hydroxyicosa-5,8,11,14-tetraenoate (18)

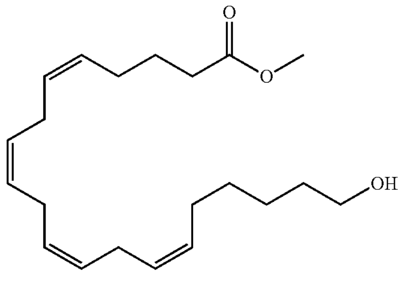 [SMILES: COC(=O)CCC/C=C\C/C=C\C/C=C\C/C=C\CCCCCO]

Partial Hydrogenation Reaction of Compound 17 to Compound 18:

It was found that the partial hydrogenation reaction of compound 17 was difficult to control without further reducing to alkane under conventional partial hydrogenation conditions (i.e., Lindlar catalyst that is further poisoned with addition of quinoline, pyridine, or ethylenediamine). To overcome the technical difficulties, it was tested whether an extra additive, 2-methyl-2-buene, can prevent undesired additional hydrogenation of compound 17. Therefore compound 17 was subject to partially hydrogenate with Lindlar catalyst, pyridine in EtOH in the presence of excess 2-methyl-2-butene. The desired compound 18, 20-HETE methyl ester, was obtained exclusively. In the presence of excess amounts of 2-methyl-2-butene, no further hydrogenation of compound 18 was occurred.

To confirm whether the method can be repeatable and scalable, the reaction was performed in duplicate (entry I, Table 1) and in a 5-fold scale (entry II, Table 1). With the exception that the reaction time was prolonged with the reaction scale, the reaction was repeatable. With these results in hand, the partial hydrogenation of both compounds 19 (see Example 3.6) and 21 (see Example 4.7) was successful in reducing multiple triple bonds to the desired cis-double bonds of 20, and 22, respectively.

TABLE 1

Partial hydrogenation of 17 to 18 (see Scheme 1)

| Scale | Compound 17 | Compound 18 | Time (h)[a] | Yield (%) |
|---|---|---|---|---|
| I | 100 mg (0.31 mmol) | 40 mg | 18 | 43[b] |
| II | 500 mg (1.55 mmol) | 250 mg | 28 | 48 |

[a]Reaction conditions: Lindlar catalyst (1 eq), 2-methyl-2-butene:EtOH:pyridine (4:4:1), room temperature, $H_2$ gas (1 atm).
[b]Average yield in duplicates.

To a solution of methyl 20-hydroxyicosa-5,8,11,14-tetraynoate (17) (0.1 g, 0.31 mmol) in 4:1 mixture of EtOH: pyridine and 2 mL of 2-methyl-2-butene was added Lindlar catalyst (0.1 g) at room temperature. The reaction mixture was stirred overnight under hydrogen atmosphere. The reaction mixture was filtered and washed with EtOAc. The filtrate was washed with water. The organic layer was dried with $MgSO_4$ and filtered. After removing the solvents in vacuo, the residue was purified by column chromatography to give the titled compound as colorless oil (48 mg, 46% yield). $^1$H NMR (400 MHz, $CDCl_3$): δ 5.42-5.30 (m, 8H), 3.66 (s, 3H), 3.63 (t, J=7 Hz, 2H), 2.86-2.76 (m, 6H), 2.31 (t, J=8 Hz, 2H), 2.13-2.02 (m, 5H), 1.70 (p, J=8 Hz, 2H), 1.61-1.51 (m, 2H), 1.42-1.32 (m, 4H). MS (ESI) m/z: 321.55 ($M+H^+$).

Example 2.8: Synthesis of (5Z,8Z,11Z,14Z)-20-Hydroxyicosa-5,8,11,14-tetraenoic acid (20-HETE)

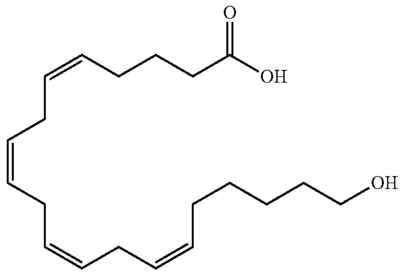

To a solution of methyl (5Z,8Z,11Z,14Z)-20-hydroxyicosa-5,8,11,14-tetraenoate (18) (16 mg, 0.05 mmol) in 2 mL of THF was added 0.1 M LiOH in water (0.5 mL) at room temperature. The reaction mixture was stirred overnight and extracted with EtOAc (2×). The combined organic layers were dried with $MgSO_4$ and filtered. The filtrate was concentrated in vacuo and purified by column chromatography to give the titled compound as colorless oil (34 mg, 88% yield). $^1$H NMR (400 MHz, $CDCl_3$): δ 5.45-5.30 (m, 8H), 3.66 (t, J=7 Hz, 2H), 2.87-2.77 (m, 6H), 2.35 (t, J=7 Hz, 2H), 2.17-2.02 (m, 5H), 1.71 (p, J=7 Hz, 2H), 1.61-1.52 (m, 2H), 1.42-1.33 (m, 4H). MS (ESI) m/z: 319.2 ($M^-$).

Example 3: Preparation of (5Z,8Z,11Z,14Z,17Z)-20-Hydroxyicosa-5,8,11,14,17-pentaenoic Acid (20-HEPE)

Example 3.1: Synthesis of 6-(Trimethylsilyl)hexa-2,5-diyn-1-ol (8)

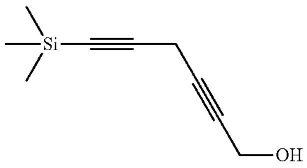

The titled compound (2.6 g, 77% yield as a colorless oil) was synthesized in a manner similar to the synthesis of the compound (5) using 4-chloro-2-butyn-1-ol (2.1 g, 20 mmol). $^1$H NMR (300 MHz, $CDCl_3$): δ 4.26 (t, J=2 Hz, 2H), 3.25 (t, J=2 Hz, 2H), 1.65 (s, 1H), 0.16 (s, 9H).

Example 3.2: Synthesis of 6-(trimethylsilyl)hexa-2,5-diyn-1-yl 4-methylbenzene-1-sulfonate (9)

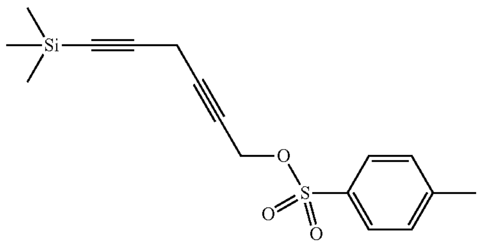

To a solution of 6-(trimethylsilyl)hexa-2,5-diyn-1-ol (8) (2 g, 12 mmol) and p-toluenesulfonyl chloride (2.75 g, 14.4 mmol) in dichloromethane were added $Et_3N$ (2.5 mL, 18 mmol) and a catalytic amounts of DMAP at 0° C. The reaction mixture was warmed up to room temperature and stirred overnight. The reaction mixture was washed with water and the organic layer was dried with $MgSO_4$. After filtering, the solvent was removed in vacuo. The residue was purified by column chromatography to give the titled compound (2.0 g, 51%) as white solid. $^1H$ NMR (300 MHz, $CDCl_3$): δ 7.82 (d, J=8 Hz, 2H), 7.35 (d, J=8 Hz, 2H), 4.70 (t, J=2 Hz, 2H), 3.11 (t, J=2 Hz, 2H), 2.46 (s, 3H), 0.16 (s, 9H).

Example 3.3: Synthesis of 10-(Trimethylsilyl)deca-3,6,9-triyn-1-ol (10)

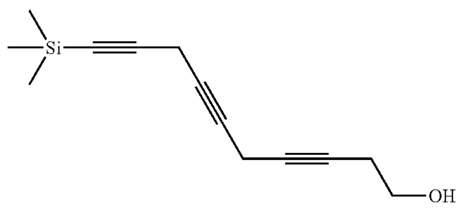

The titled compound (0.63 g, 50% yield as a colorless oil) was synthesized in a manner similar to the synthesis of the compound (5) using 3-butyn-1-ol (0.41 g, 5.8 mmol) and the compound (9) (1.9 g, 5.8 mmol). $^1H$ NMR (400 MHz, $CDCl_3$): δ 3.70 (t, J=6 Hz, 2H), 3.22-3.19 (m, 2H), 3.18-3.14 (m, 2H), 2.47-2.41 (m, 2H), 1.77 (s, 1H), 0.16 (s, 9H).

Example 3.4: Synthesis of deca-3,6,9-triyn-1-ol (11)

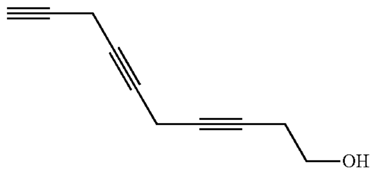

The titled compound (0.22 g, 85% as clear oil) was prepared in a manner similar to the synthesis of the compound (6) using the compound (10) (0.4 g, 1.8 mmol). $^1H$ NMR (400 MHz, $CDCl_3$): δ 3.71 (t, J=6 Hz, 2H), 3.19-3.13 (m, 4H), 2.47-2.42 (m, 2H), 2.09 (s, 1H), 2.07 (t, J=3 Hz, 1H).

Example 3.5: Synthesis of Methyl 20-hydroxyicosa-5,8,11,14,17-pentaynoate (19)

The titled compound (0.15 g, 40% as yellowish oil) was prepared in a similar to the synthesis of the compound (17) from the compound (11) (0.17 g, 1.2 mmol) and the compound (3) (0.33 g, 1.3 mmol). $^1H$ NMR (400 MHz, $CDCl_3$): δ 3.70 (t, J=6 Hz, 2H), 3.67 (s, 3H), 3.17-3.10 (m, 8H), 2.48-2.36 (m, 4H), 2.26-2.19 (m, 2H), 1.81 (p, J=7 Hz, 2H).

Example 3.6: Synthesis of Methyl (5Z,8Z,11Z,14Z,17Z)-20-hydroxyicosa-5,8,11,14,17-pentaenoate (20)

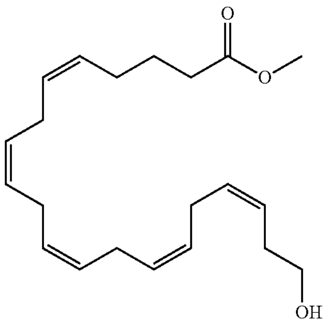 [SMILES: COC(=O)CCC/C=C\C/C=C\C/C=C\C/C=C\C/C=C\CCO]

The titled compound (46 mg, 45% as yellowish oil) was prepared in a similar to the synthesis of the compound (18) from the compound (19) (0.1 g, 0.31 mmol) except the reaction mixture was stirred for 3 days in EtOAc instead of EtOH. $^1H$ NMR (400 MHz, $CDCl_3$): δ 5.62-5.30 (m, 10H), 3.70-3.60 (m, 2H), 3.67 (s, 3H), 2.90-2.75 (m, 8H), 2.40-2.29 (m, 4H), 2.11 (dd, J=14 and 7 Hz, 2H), 1.71 (p, J=7 Hz, 2H), 1.58 (s, 1H). MS (ESI) m/z: 381.60 ($M+Na^+$).

Example 3.7: The synthesis of (5Z,8Z,11Z,14Z,17Z)-20-Hydroxyicosa-5,8,11,14,17-pentaenoic acid (20-HEPE)

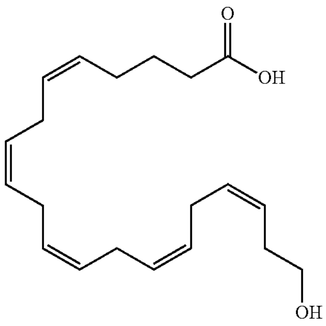 [SMILES: O=C(O)CCC/C=C\C/C=C\C/C=C\C/C=C\C/C=C\CCO]

The titled compound (8 mg, 50% as yellowish oil) was prepared in a similar to the synthesis of the compound 20-HETE from the compound (20) (16.7 mg, 0.05 mmol). $^1H$ NMR (400 MHz, $CDCl_3$): δ 5.63-5.31 (m, 10H), 3.77-

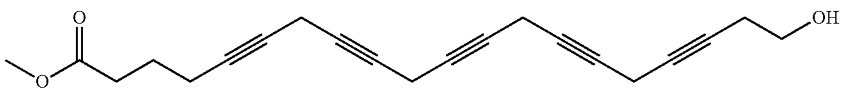

3.61 (m, 2H), 2.94-2.75 (m, 8H), 2.43-2.32 (m, 4H), 2.14 (dd, J=14 and 7 Hz, 2H), 1.71 (q, J=7 Hz, 2H). MS (ESI) m/z: 317.2 (M).

Example 4: preparation of (4Z,7Z,10Z,13Z,16Z,19Z)-22-Hydroxydocosa-4,7,10,13,16,19-hexaenoic acid (22-HDoHE)

Example 4.1: Synthesis of Methyl pent-4-ynoate (12)

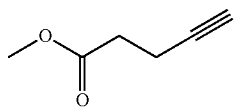

The titled compound (2.86 g, 50% as yellowish oil) was prepared in a similar to the synthesis of the compound (18) from the compound (19) (5 g, 51 mmol). $^{1}H$ NMR (400 MHz, DMSO-$d_6$): δ 3.62 (s, 3H), 2.81-2.80 (m, 1H), 2.54-2.49 (m, 2H), 2.42-2.39 (m, 2H).

Example 4.2: Synthesis of Methyl 9-hydroxynona-4,7-diynoate (13)

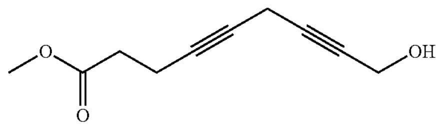

The titled compound (1.35 g, 75% as yellowish oil) was prepared in a similar to the synthesis of the compound (2) from the compound (12) (1.12 g, 10 mmol). $^{1}H$ NMR (400 MHz, $CDCl_3$): δ 4.26 (t, J=2 Hz, 2H), 3.70 (s, 3H), 3.17 (p, J=2 Hz, 2H), 2.55-2.45 (m, 4H). OH peak is missing.

Example 4.3: Synthesis of Methyl 9-bromonona-4,7-diynoate (14)

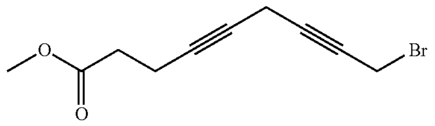

The titled compound (0.65 g, 75% yield) was prepared in a similar to the synthesis of the compound (13) (0.65 g, 3.6 mmol). $^{1}H$ NMR (400 MHz, $CDCl_3$): δ 3.90 (t, J=2 Hz, 2H), 3.69 (s, 3H), 3.19 (p, J=2 Hz, 2H), 2.55-2.45 (m, 4H).

Example 4.4: The synthesis of Methyl 12-hydroxydodeca-4,7,10-triynoate (15)

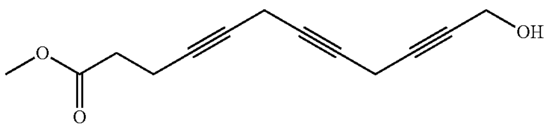 [SMILES: COC(=O)CCC#CCC#CCC#CCO]

The titled compound (0.55 g, 94% as yellowish oil) was prepared in a similar to the synthesis of the compound (2) from the compound (14) (0.65 g, 2.67 mmol). $^{1}H$ NMR (400 MHz, $CDCl_3$): δ 4.26-4.24 (m, 2H), 3.69 (s, 3H), 3.21-3.17 (m, 2H), 3.13-3.09 (m, 2H), 2.55-2.44 (m, 4H), 1.71 (s, 1H).

Example 4.5: Synthesis of Methyl 12-bromododeca-4,7,10-triynoate (16)

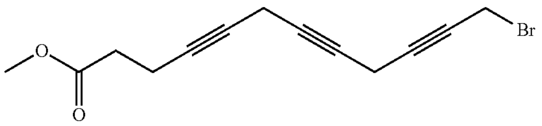 [SMILES: COC(=O)CCC#CCC#CCC#CCBr]

The titled compound (0.35 g, 50% yield) was prepared in a similar to the synthesis of the compound (15) (0.54 g, 2.5 mmol). $^{1}H$ NMR (300 MHz, $CDCl_3$): δ 3.90 (t, J=2 Hz, 2H), 3.69 (s, 3H), 3.22 (q, J=2 Hz, 2H), 3.12 (t, J=2 Hz, 2H), 2.56-2.44 (m, 4H).

Example 4.6: Synthesis of Methyl 22-hydroxydocosa-4,7,10,13,16,19-hexaynoate (21)

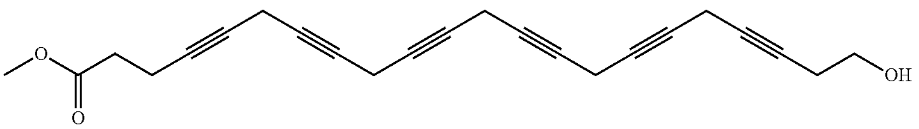 [SMILES: COC(=O)CCC#CCC#CCC#CCC#CCC#CCC#CCCO]

The titled compound (0.1 g, 58% as yellowish oil) was prepared in a similar to the synthesis of the compound (17) from the compound (11) (0.073 g, 0.5 mmol) and the compound (16) (0.15 g, 0.55 mmol). $^{1}H$ NMR (400 MHz, $CDCl_3$): δ 3.71 (t, J=6 Hz, 2H), 3.70 (s, 3H), 3.17-3.10 (m, 10H), 2.56-2.42 (m, 6H), 1.74 (s, 1H).

Example 4.7: The synthesis of Methyl (4Z,7Z,10Z,13Z,16Z,19Z)-22-hydroxydocosa-4,7,10,13,16,19-hexaenoate (22)

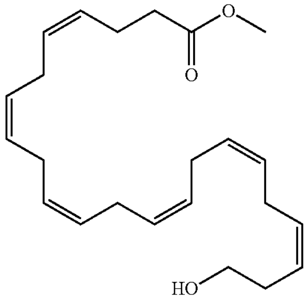 [SMILES: COC(=O)CC/C=C\C/C=C\C/C=C\C/C=C\C/C=C\C/C=C\CCO]

The titled compound (0.04 mg, 50% as yellowish oil) was prepared in a similar to the synthesis of the compound (18) from the compound (21) (0.08 g, 0.23 mmol) except the reaction mixture was stirred for 3 days in EtOAc instead of EtOH. $^{1}H$ NMR (400 MHz, $CDCl_3$): δ 5.60-5.29 (m, 1H), 3.67 (s, 1H), 3.66 (t, J=7 Hz, 2H), 2.90-2.78 (m, 1H), 2.42-2.32 (m, 1H), 1.51 (s, 1H). MS (ESI) m/z: 381.60 $(M+H^+)$.

Example 4.8: Synthesis of (4Z,7Z,10Z,13Z,16Z,19Z)-22-Hydroxydocosa-4,7,10,13,16,19-hexaenoic acid (22-HDoHE)

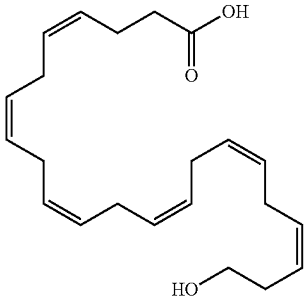 [SMILES: O=C(O)CC/C=C\C/C=C\C/C=C\C/C=C\C/C=C\C/C=C\CCO]

The titled compound (7.5 mg, 78.5% as yellowish oil) was prepared in a similar to the synthesis of the compound 20-HETE from the compound (20) (10 mg, 0.028 mmol). $^{1}H$ NMR (400 MHz, $CDCl_3$): δ 5.60-5.29 (m, 1H), 3.67 (s, 1H), 3.66 (t, J=7 Hz, 2H), 2.90-2.78 (m, 1H), 2.42-2.32 (m, 1H), 1.51 (s, 1H). MS (ESI) m/z: 343.2 (M).

Example 5: Characterization of Prepared 20-HETE, 20-HEPE, and 22-HDoHE

The structure and purity of purified 20-HETE were further assessed by LC-MS/MS. The hydrolyzed sophorolipids or isolated 20-HETE was dissolved in methanol or acetonitrile to prepare a 1 mg/ml solution, then diluted 1,000-4,000 times for LC-MS/MS analysis. The solutions were injected into a LC-MS/MS system, including Agilent 1200SL (Santa Clara, Calif.) system coupled to AB Sciex 4000 QTrap system (Foster City, Calif.). The LC/MS/MS method was described in Reference 37. The mass spectrometer was operated under negative electrospray mode. The MRM transition for 20-HETE, 20-HEPE, and 22-HDoHE were 319.2/275.2, 317.2/255.0, and 343.2/281.1, respectively. Other parameters for 20-HETE were DP-60 V, CE-26, and CXP-8. In addition, the identification of synthesized 20-HETE was implemented by comparing with 20-HETE and 20-HETE-$d_6$ standard.

Figure 2A:
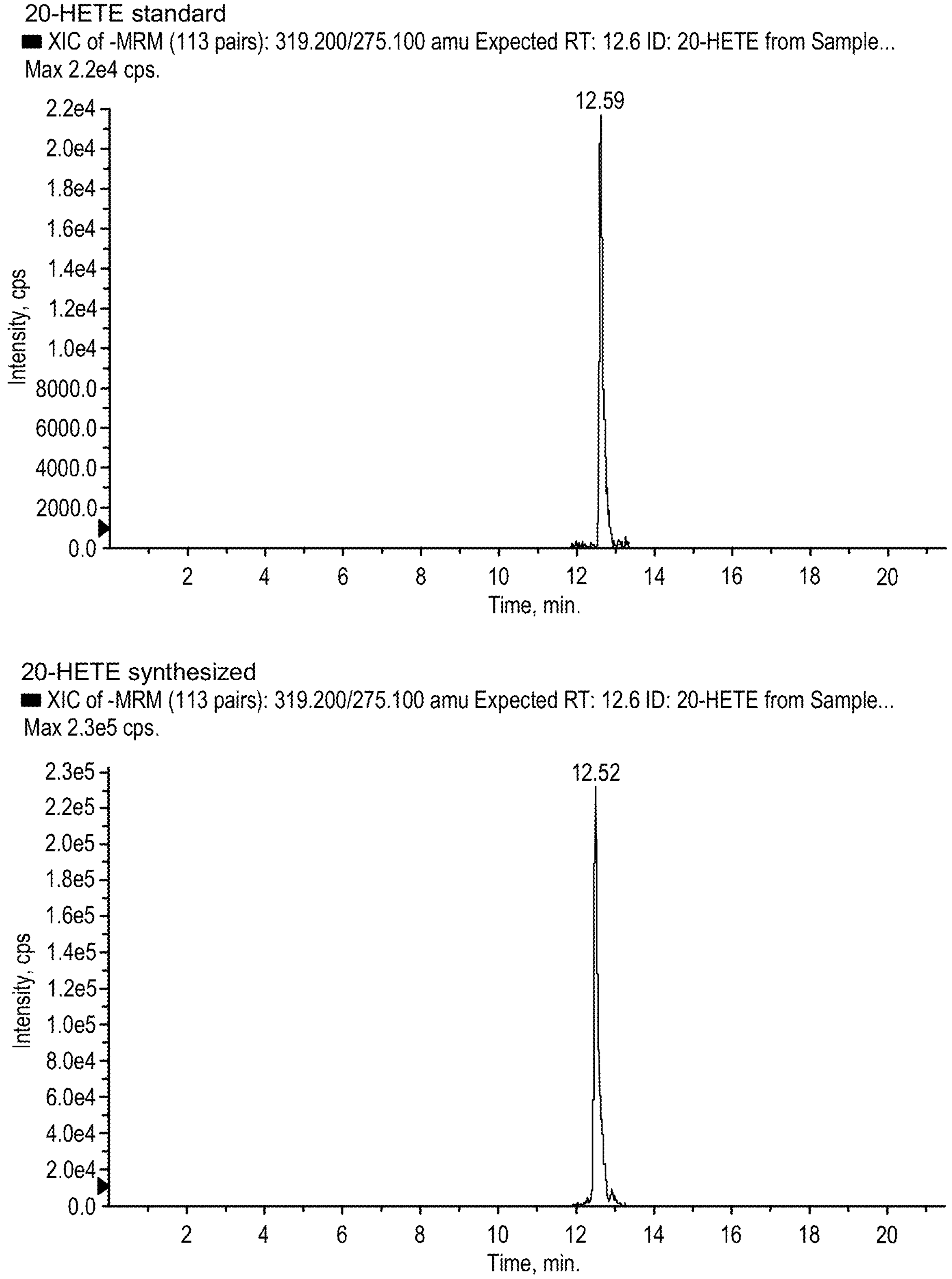
FIG. 2A shows LC-MS/MS analysis of 20-hydroxyeicosatetraenoic acid (20-HETE) from a commercial source vs. synthesized.
Figure 2B:
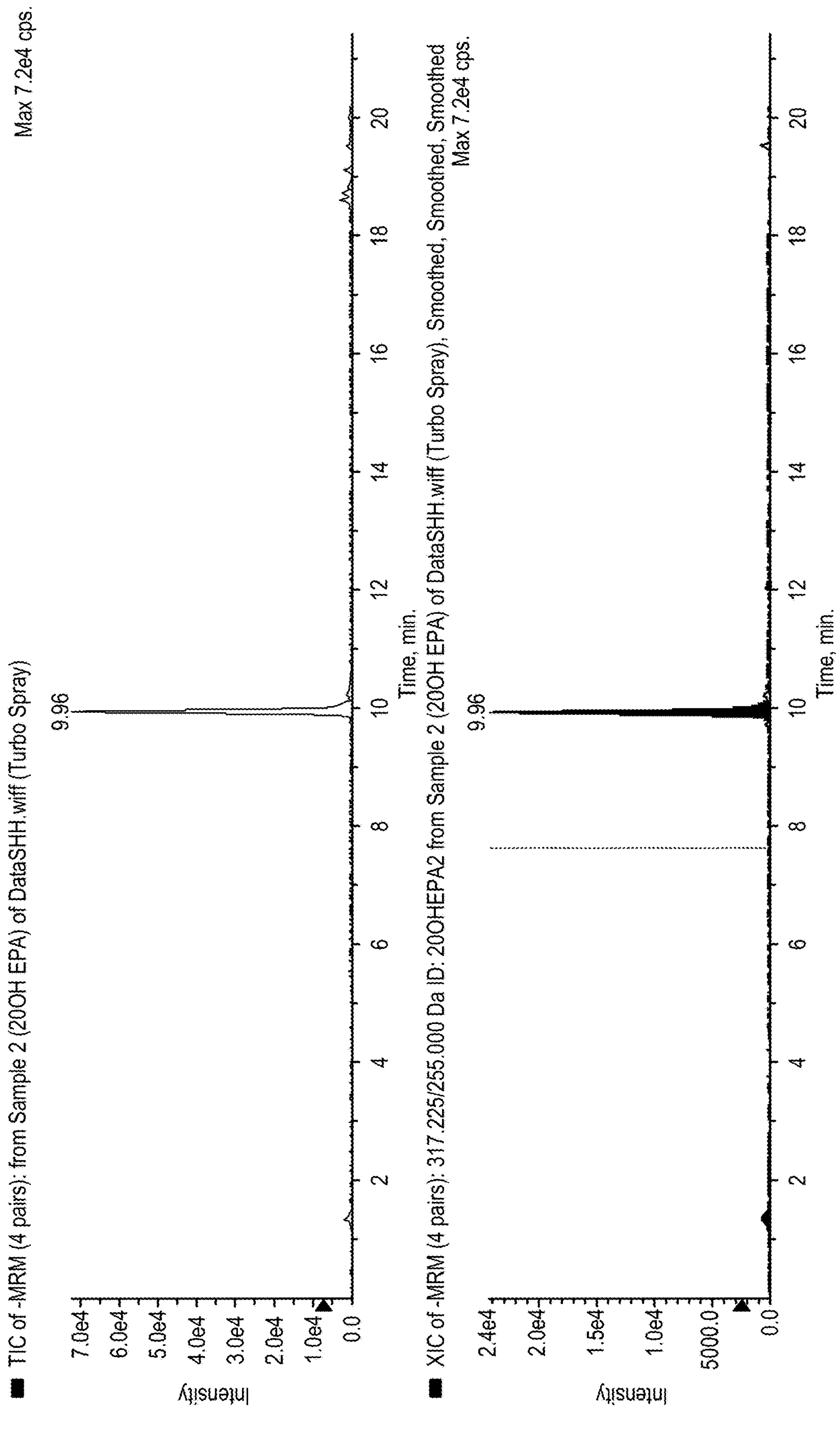
FIG. 2B shows LC-MS/MS analysis of 20-hydroxyeicosapentaenoic acid (20-HEPE).
Figure 2C:
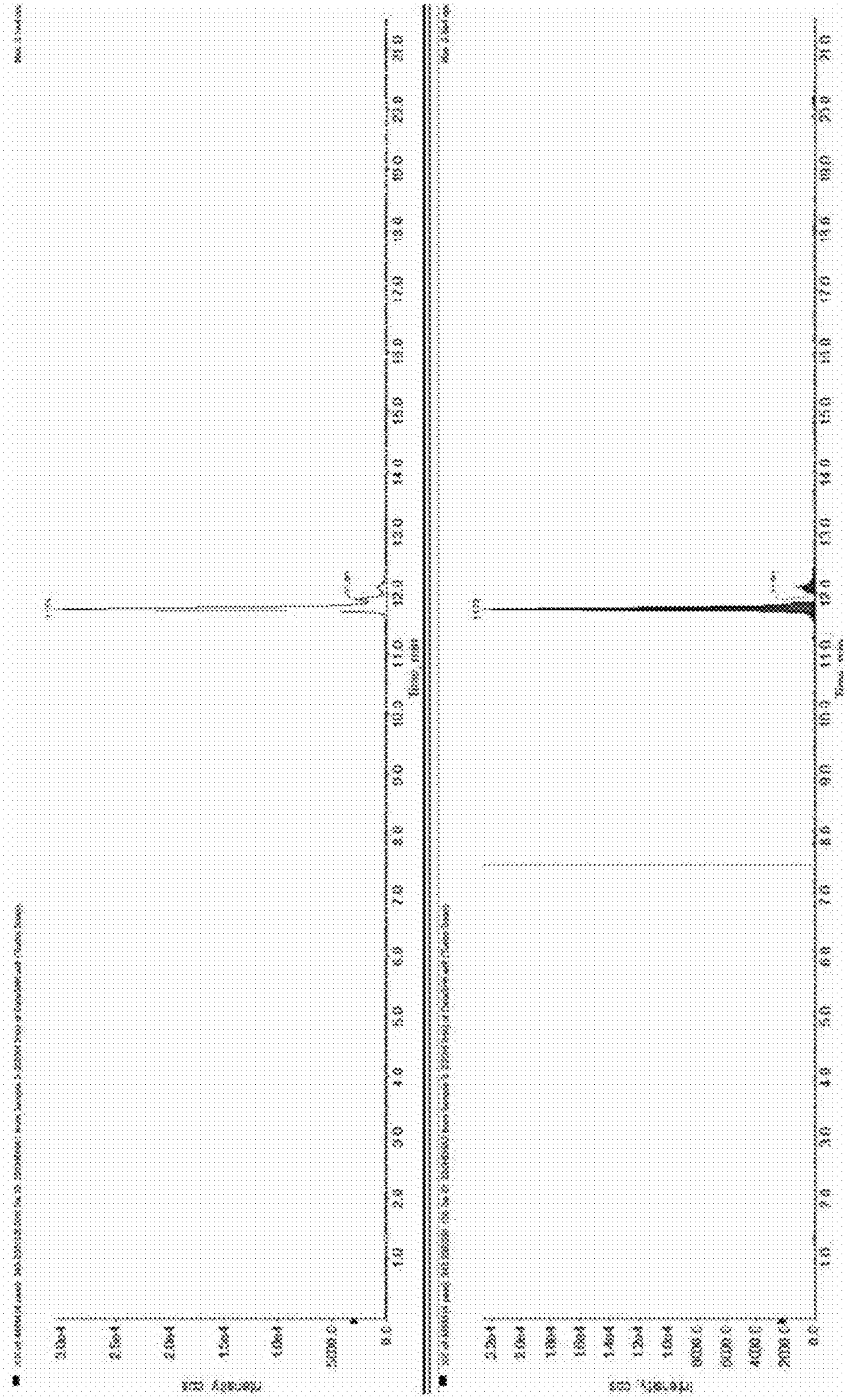
FIG. 2C shows LC-MS/MS analysis of 22-HDoHE. Extracted-ion chromatogram (XIC): 319.2/275.1 for 20-HETE, 317.2/255.0 for 20-HEPE, and 343.2/281.1 for 22-HDoHE, respectively.
Figure 3:
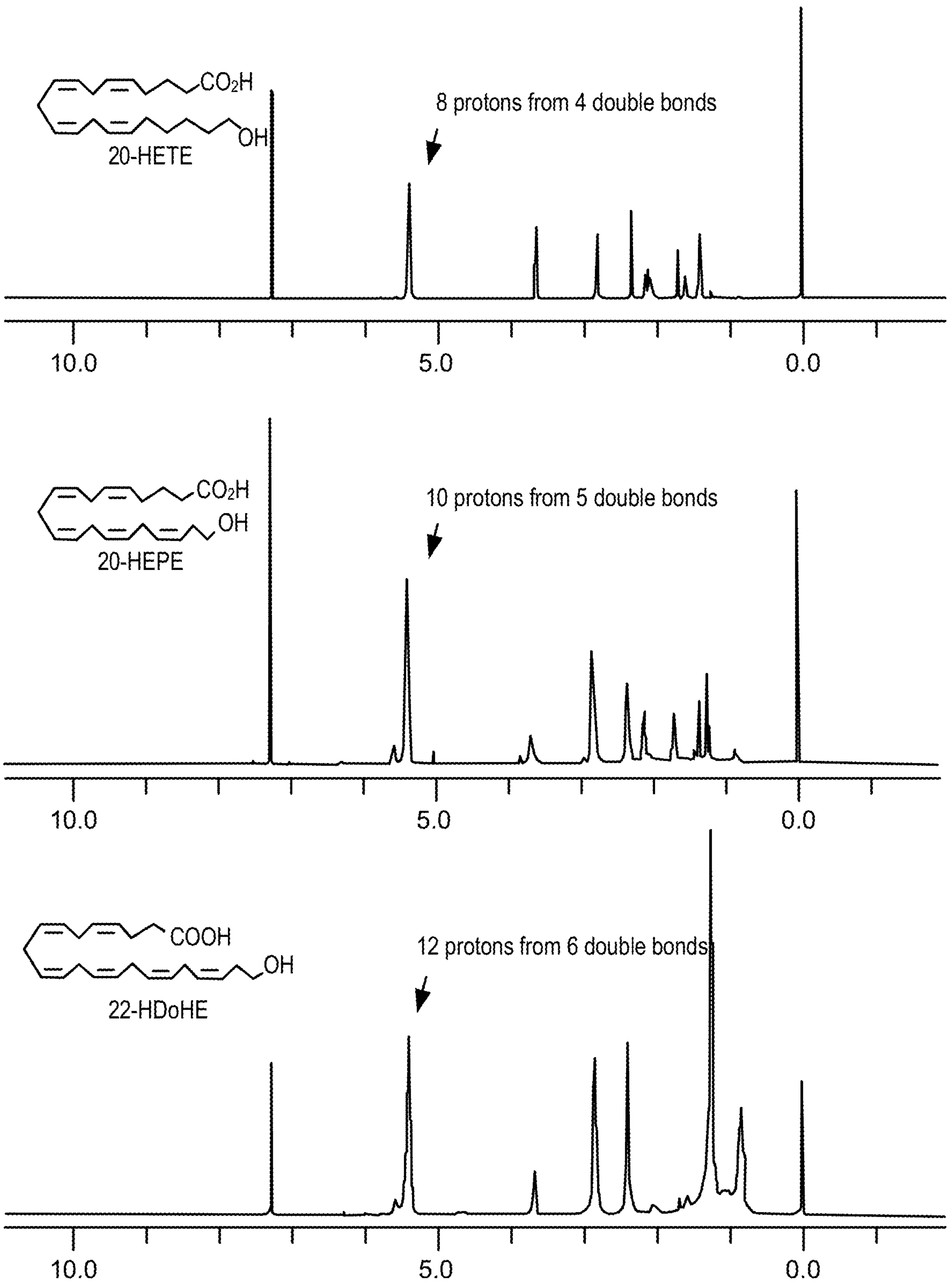
FIG. 3 is $^1$H NMR spectra of 20-HETE, 20-HEPE, and 22-HDoHE.

The purity and identification of 20-HETE, 20-HEPE, and 22-HDoHE, evaluated by LC-MS/MS, is shown in FIG. 2. $^{1}H$ NMR spectra of 20-HETE, 20-HEPE, and 22-HDoHE are shown in FIG. 3. As shown in FIG. 2A, the synthesized 20-HETE have the same retention time and the mass compared to the commercial 20-HETE (>98% of purity). The purity of 20-HETE (95.1% of purity), 20-HEPE (91.3% of purity) or 22-HDoHE (94.6% of purity) was determined by comparison of observed mass and calculated mass. 20-HETE was found to have a purity of 95.1%; 20-HEPE was found to have a purity of 91.3%; and 22-HDoHE was found to have a purity of 94.6%; accordingly.

Example 6: Study of 20-HETE, 20-HEPE, and 22-HDoHE for their Activation of TRPV1 In Vitro mTRPV1 Plasmid and HEK-293 Cells:

The mTRPV1 plasmid that contains a GFP tag was a generous gift from Professor Jie Zheng at University of California, Davis. The HEK-293 cells were cultured in a poly-D-lysine coated T75 dish at an initial density of $4\times10^5$ cells/dish and maintained in culture medium (DMEM+10% FBS+100 units/ml penicillin, 0.1 mg/ml streptomycine) in an incubator at 37° C. with 5% $CO_2$ and 95% humidity. At 50% confluence, the HEK-293 cells were transfected with 10 μg of mTRPV1 plasmid using Lipofectamine 2000 (Invitrogen Corporation, Carlsbad, Calif., USA) in antibiotic—as well as serum-free culture medium. After 6 hour incubation, the serum-free medium was replaced with normal culture medium and the cells were cultured for another 48 hours. The transfection efficiency was determined by examined the GFP expression as well as the $Ca^{2+}$ response after exposure to capsaicin.

The HEK-293 cells transiently transfected mTRPV1 were planted onto poly-D-lysine (Sigma-Aldrich, St. Louis, Mo., USA) coated black-well, clear-bottom, 96-well plates (Corning, Coring, N.Y., USA) at an initial density of 40,000/well. The cells were then cultured in DMEM medium for 18-24 hours as described previously (Ref. 38). Briefly, the growth medium was removed and replaced with dye loading buffer (100 μl/well) containing 4 μM fluo-4 and 0.5 mg/ml BSA in Locke's buffer (in mM: 8.6 HEPES, 5.6 KCl, 154 NaCl, 5.6 Glucose, 1.0 $MgCl_2$, 2.3 $CaCl_2$), 0.0001 glycine, pH 7.4). After 1 hour incubation in dye loading buffer, cells were washed four times in fresh Locke's buffer and transferred to the plate chamber of FLIPR$^{TETRA}$ (Molecular Devices, Sunnyvale, Calif., USA). The final volume of Locke's buffer in each well was 150 μl. The cells were excited at 488 nm and $Ca^{2+}$ bound fluo-4 emission at 535 nm was recorded. Fluorescence readings were taken every 1 second for 120 s to establish the baseline. Different concentrations (4×) of compounds were added to the cells from a compound plate in a volume of 50 μl at a rate of 30 μl/s using a programmable robotic system. The fluorescence signals were recorded for an additional 380 seconds. All the experiments were performed at room temperature. The $Ca^{2+}$ data were represented as Fluo-4 fluorescence units ($F/F_0$). For quantifying the $Ca^{2+}$ response, the area under the curve (AUC) was used. Graphing and statistical analyses were performed using GraphPad Prism software (GraphPad Software Inc., San Diego, Calif.). Statistical significance was determined by an ANOVA and, where appropriate, a Dunnett's multiple comparison test and p values below 0.05 was considered statistically significant.

In vitro Study of ω-Hydroxylated Polyunsaturated Fatty Acids for Activation of mTRPV1

The influence of 20-HETE, 20-HEPE, and 22-HDoHe on mTRPV1 was measured in HEK293 cells heterologously expressed mTRPV1 using calcium influx assay. Capsaicin was applied to stimulate the $Ca^{2+}$ influx in mTRPV1 expressed HEK293 cells as a positive control, shown in FIG. 4. It was found that 22-HDoHE (~3 μM concentration) produced significant $Ca^{2+}$ influx and 20-HEPE produced significant $Ca^{2+}$ influx at 10 μM. However, 20-HETE produced marginal $Ca^{2+}$ response at the concentrations examined (see FIG. 4). It is worth noting that 20-HETE at 10 μM concentration activates hTRPV1 in a previous study (Ref 24). The discrepancy between previous study and current study is likely due to the fact that the mTRPV1 was used in the current study, while the hTRPV1 was used in the previous study. Nevertheless, the current data has demonstrated that both 20-HEPE and 22-HDoHE may be more potent (or more efficacious) to stimulate mTRPV1 than 20-HETE does.

Figure 4A:
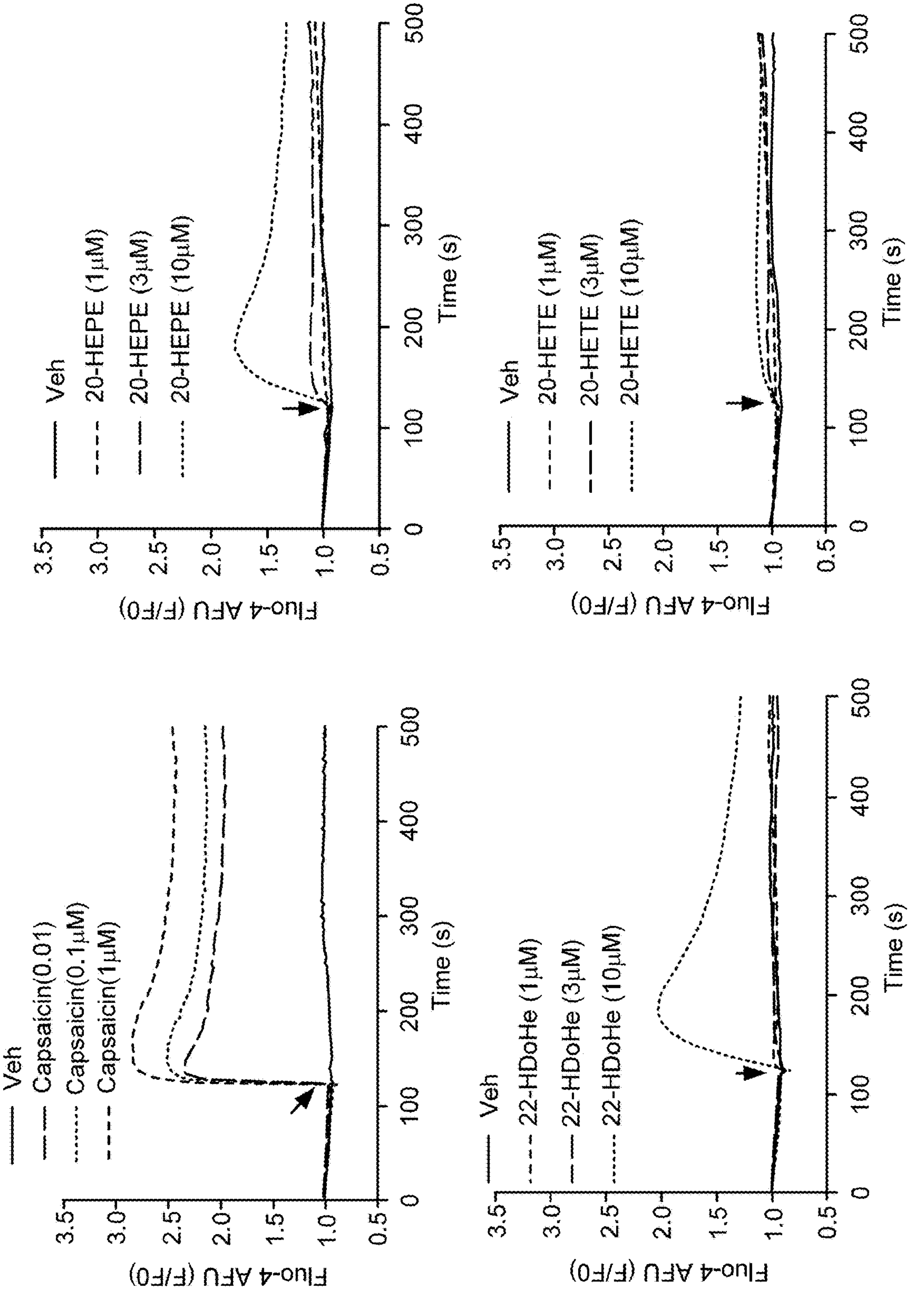
FIG. 4A is a set of graphs of calcium influx in heterologously expressed mTRPV1 as a function of time induced by capsaicin, 20-HEPE, 22-HDoHE and 20-HETE.
Figure 4B:
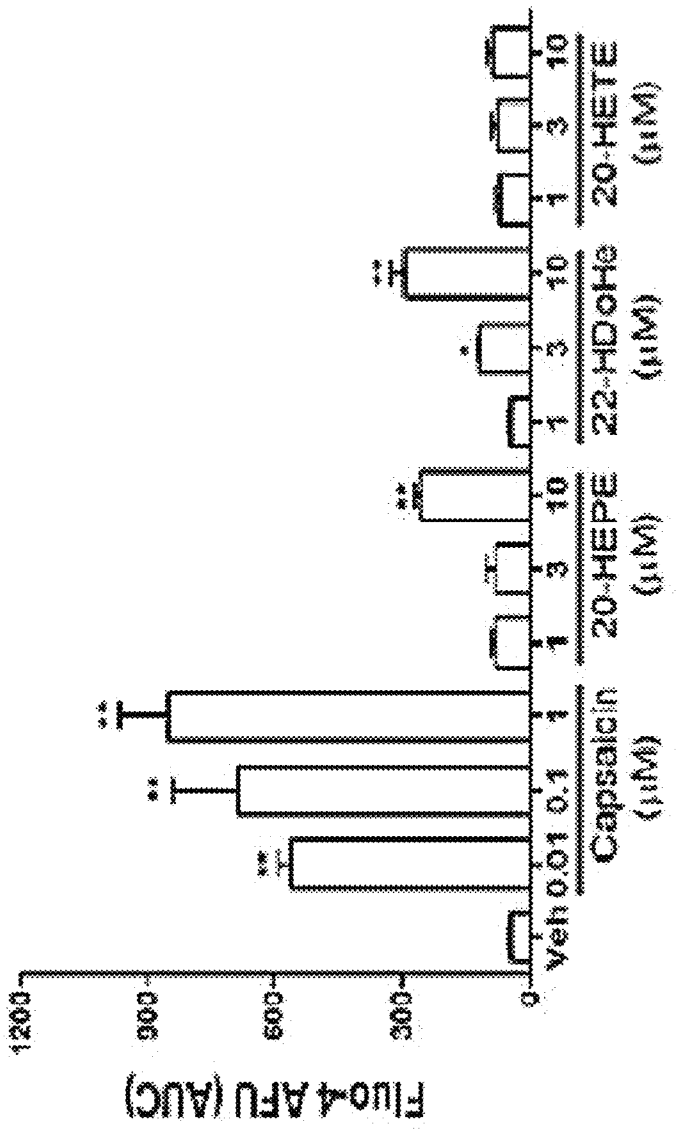
FIG. 4B is a bar graph of the quantification of the $Ca^{2+}$ responses (area under curve, AUC) induced by capsaicin, 20-HEPE, 22-HDoHE and 20-HETE.

As shown in FIG. 4, 20-HETE does not appear to be an mTRPV1 activator at or below concentration of 10 uM. Similarly, 20-HEPE and 22-HDoHE did not activate TRPV1 channels at low doses. However the ω-3 metabolites demonstrated activity at the highest dose of 10 μM but with far less signal than a low dose of the classical agonist capsaicin.

Example 7: Study of 20-HETE, 20-HEPE, and 22-HDoHE for Inhibition of COXs

In addition, 20-HETE, but not 20-HEPE or 22-HDoHE, has been known to be metabolized by cyclooxygenases (COXs) to form 20-hydroxy PGE2 (20-OH PGE2), which is merely known as a vasodilator (see Ref 29)

Figure 5:
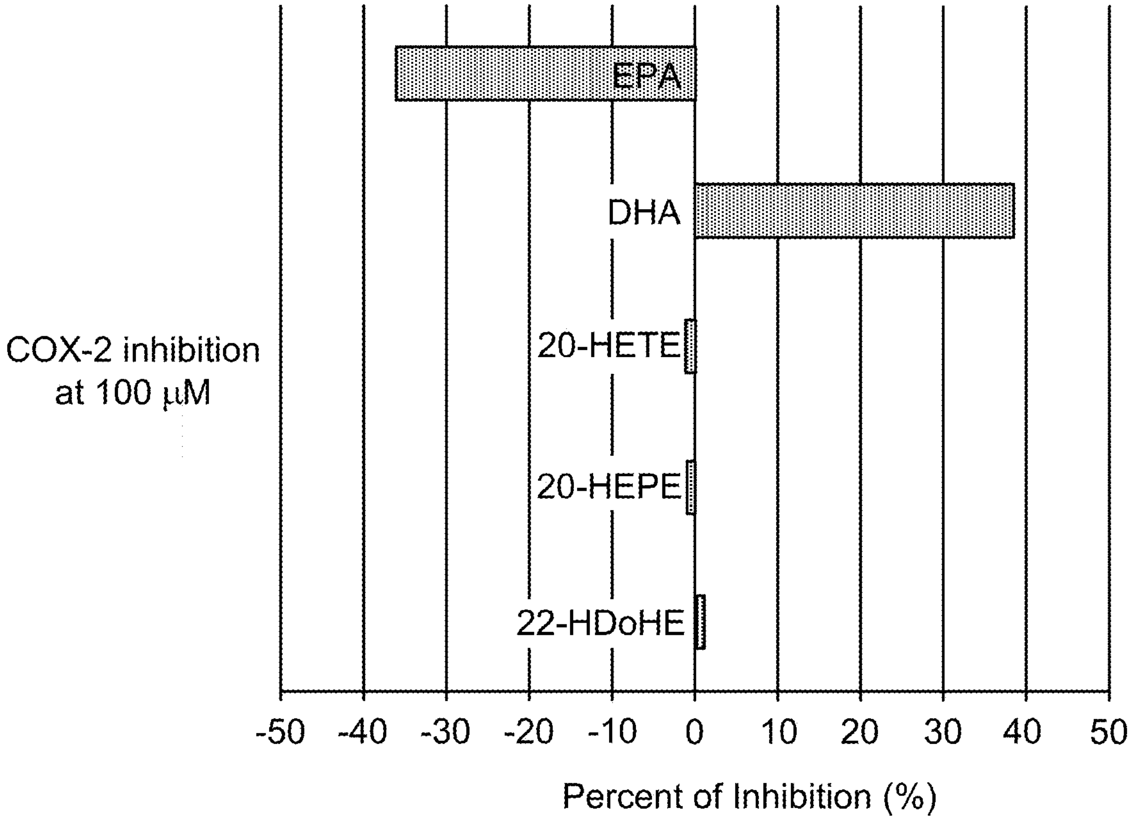
FIG. 5 is a bar graph of the COX inhibitory activity of 20-HETE, 20-HEPE and 22-HDoHE. Less than 0% inhibition was obtained with eicosapentaenoic acid (EPA), suggesting that EPA is a substrate for COX-2.

Percent inhibition at 100 μM of 20-HETE, 20-HEPE, and 22-HDoHe against ovine COX-1 and human COX-2 was determined using a COX Fluorescent Inhibitor Screening Assay Kit (catalog number 700100, Cayman Chemical, Ann Arbor, Mich.) according to the manufacturer's instructions. Briefly, to a series of supplied reaction buffer solutions (150 μl, 100 mM Tris-HCl, pH 8.0) with either COX-1 or COX-2 (10 μl) enzyme in the presence of Heme (10 μl) and fluorometric substrate (10 μl) were added 10 μl of 100 μM concentration of the test compound solutions. The reactions were initiated by adding 10 μl of ARA solution and then incubated for two minutes at room temperature. Percent inhibition was calculated by comparison from the 100% initial activity sample value (no inhibitor). Results were determined by the test run in triplicate, shown in Table 2. No COX-2 activity changes have been found up to 100 μM concentrations, as shown in FIG. 5.

TABLE 2

Inhibition of 20-HETE, 20-HEPE, and 22-HDoHe against COX-1 and COX-2 enzymes

| | % inhibition at 100 μM | |
|---|---|---|
| | COX-1 | COX-2 |
| Indomethacin | 87 | — |
| celecoxib | — | 99 |
| 20-HETE | 27.5 | 0 |
| 20-HEPE | 37.1 | 0 |
| 22-HDoHe | 38.1 | 1 |

Example 8: Study of Mechanical Allodynia In Vivo Induced by 20-HETE, 20-HEPE, and 22-HDoHE Male Sprague-Dawley rats weighing approximately 250-300 grams were obtained from Charles River Laboratories. On the day of the test, rats were brought to the testing apparatus and allowed to acclimate. The apparatus is a raised metal mesh platform with clear acrylic chambers to enclose rats but allow them to move freely. After 30 minutes the rats were tested with a von Frey aesthesiometer for their non-treated baseline withdrawal thresholds using a rigid tip on the plantar surface of the rat hind paw though the mesh floor. The scores are grams of force applied to the hind paw required to elicit a withdrawal. The pretreatment baseline score was considered the pain-free baseline (BL) and was assigned 100% for further response calculations.

For the pain assay, 20-HETE methyl ester, 20-HEPE methyl ester, or 22-HDoHE methyl ester, formulated in 10% EtOH in saline, were injected intraplantar in naïve rats. Withdrawal thresholds were measured at 15, 30, 60, 90, 120 and 150 minutes post injection. Reported scores are calculated as a percent of the pretreatment baseline score with an average of 6 rats (3 trials per rat) with SEM for the group.

Figure 6A:
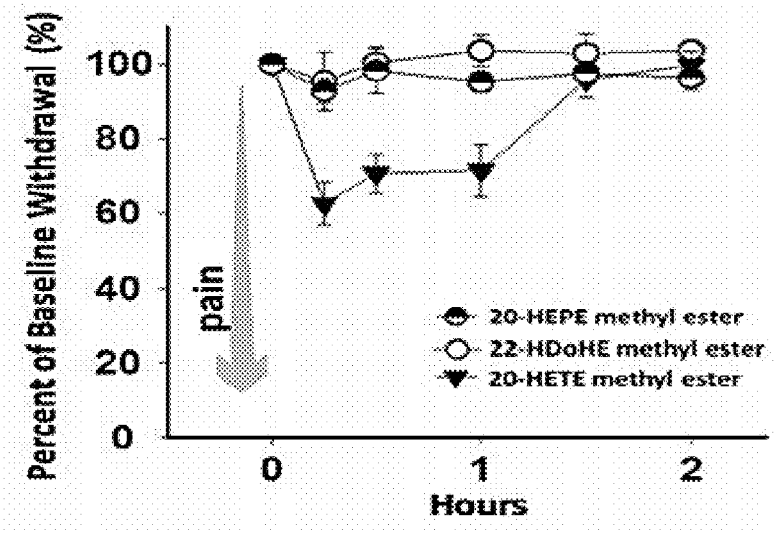
FIG. 6A is a graph showing results of von Frey mechanical nociceptive assays.
Figure 6B:
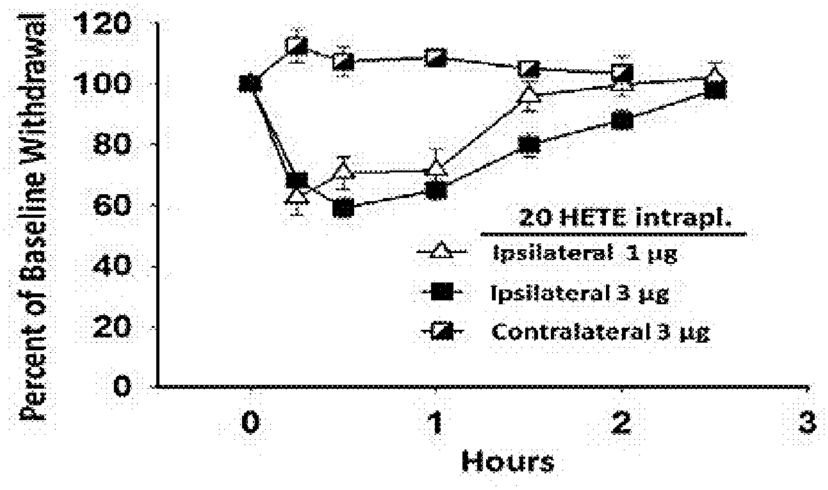
FIG. 6B is a graph showing a dose-response manner only with ipsilateral administration of 20-HETE.

The methyl esters compounds of 20-HETE, 20-HEPE and 22-HDoHE were tested for their ability to induce mechanical allodynia in vivo. For the assay, naïve rats were injected intraplantar with 1 μg of each ester and tested with an electronic von Frey aesthesiometer. The results are shown in FIG. 6A. 20-HETE decreased nociceptive thresholds acutely in naïve rats and in a dose-response manner only with ipsilateral administration, as shown in FIG. 6B. However neither 20-HEPE nor 22-HDoHE induced a similar decrease in thresholds.

As shown in Example 6, both 20-HEPE and 22-HDoHE are potent TRPV1 agonist but not a pain inducer like 20-HETE in vivo.

Example 9: The Effect of 22-HDoHE on Angiogenesis

Figure 7A:
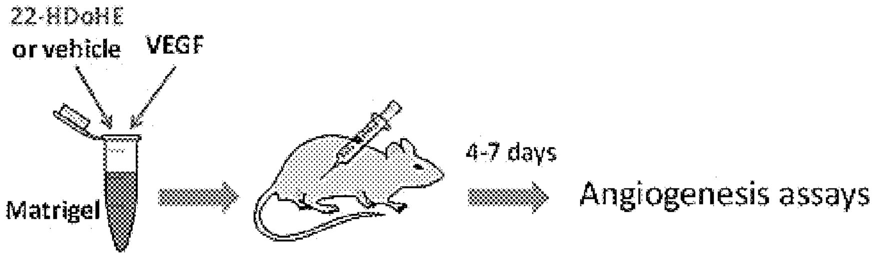
FIG. 7A is a simplified scheme of the animal experiment: Matrigel containing VEGF (angiogenesis inducer) and 22-HDoHE or vehicle were injected into C57BL/6 mice, after 4-7 days of treatment, the Matrigel plugs were dissected and subjected to angiogenesis analysis.
Figure 7B:
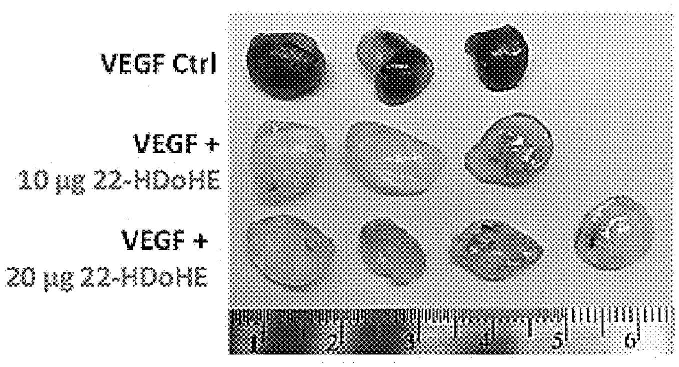
FIG. 7B is representative images of dissected Matrigel plugs: in the VEGF control (positive control), Matrigels had strong infiltration of blood into the plugs, which were abolished by the 22-HDoHE treatment.
Figure 7C:
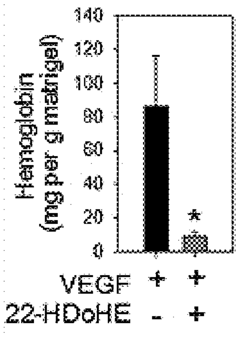
FIG. 7C is a quantification of angiogenesis in the dissected Matrigel plugs, which showed that 22-HDoHE strongly inhibited VEGF-induced angiogenesis in vivo.

Anti-Angiogenic Action of 22-HDoHE In Vivo:

Angiogenesis, the process of formation of new blood vessels from pre-existing vessels, has been established to be critical for multiple human diseases including cancer. The effect of 22-HDoHE on angiogenesis was examined using a Matrigel plug assay in C57BL/6 mice, as shown in FIG. 7A. Vascular endothelial growth factor (VEGF) is the most important angiogenesis inducer. Implantation of Matrigel plugs containing 100 ng VEGF in mice triggered a robust angiogenic response, while ω-addition of 22-HDoHE in the Matrigel almost abolished VEGF-induced angiogenesis, demonstrating the anti-angiogenic action of 22-HDoHE in vivo, as shown in FIG. 7B.

Figure 8:
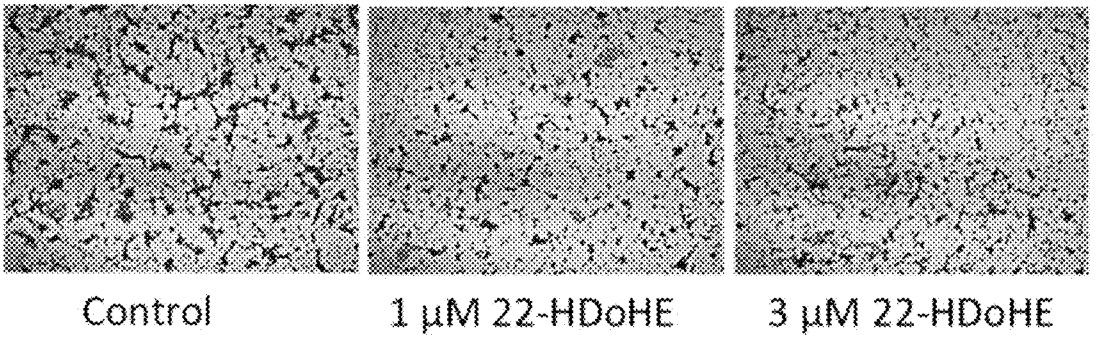
FIG. 8 is a series of photographs showing 22-HDoHE inhibition of VEGF-induced endothelial cell migration in HUVEC cells. The cell migration assay was conducted using a standard Boyden chamber assay with 10 ng/mL VEGF as chemoattractant, and the assay time was 6 hours.

Anti-Angiogenic Action of 22-HDoHE In Vitro:

It was tested whether 22-HDoHE has direct anti-angiogenic actions in primary endothelial cells, using a VEGF-induced endothelial cell migration in human umbilical vein endothelial cells (HUVECs). At a dose range of 1-3 μM, 22-HDoHE significantly inhibited VEGF-induced HUVECs migration, demonstrating its anti-angiogenic activity in vitro. The results are shown in FIG. 8.

Example 10: The Effect of 22HDoHE on Primary Tumor Growth

Figure 9:
FIG. 9 is a photograph and a bar graph showing systematic treatment of 0.5 mg/kg/day 22-HDoHE inhibited ~50% of B16F10 melanoma growth in C57BL/6 male mice. B16F10 melanoma cells (200,000 cells per mouse) were sub-Q injected into C57BL/6 mice to induce primary tumor growth of melanoma, then the mice were treated with 22-HDoHE using mini-pumps at a dose of 0.5 mg/kg/day. After 2-wk treatment, the mice were sacrificed to dissect the tumors for analysis.

Angiogenesis has been well established to play an essential role in cancer, through providing nutrients and oxygen to the tumors tissues to promote tumor progression. The effect of 22HDoHE on primary tumor growth in mice was studied using a highly aggressive B16F10 melanoma model in C57BL/6 mice. Treatment with 0.5 mg/kg/day 22-HDoHE caused an approximate 50% reduction of B16F10 tumor growth in mice, demonstrating its anti-cancer effects in vivo. The results are shown in FIG. 9.

Example 11: The Effect of 22HDoHE on Lymphangiogenesis

Figure 10:
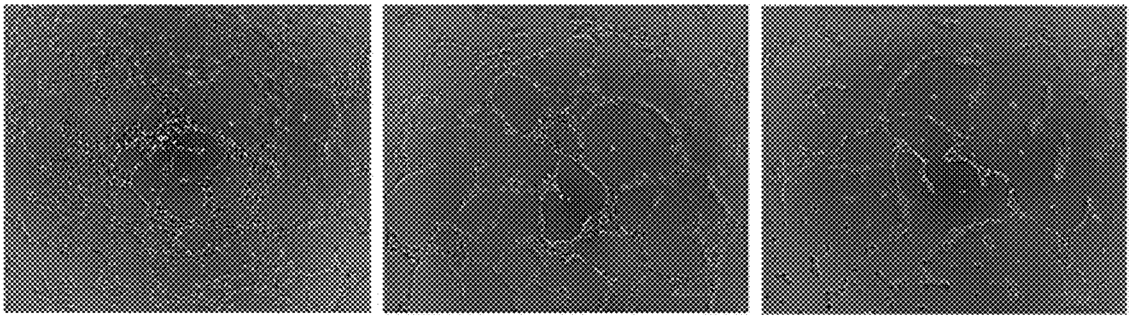
FIG. 10 is a series of photographs showing treatment with 22-HDoHE inhibits tube formation in HMVEC-dLy cells.

Lymphangiogenesis has been shown to play a critical role in tumor metastasis and many other human diseases. The effect of 22-HDoHE on lymphangiogenesis was evaluated using a vascular endothelial growth factor-C (VEGF-C)-induced tube formation in human dermal lymphatic endothelial cells (HMVEC-dLy). The result showed that 22-HDoHE significantly inhibited VEGF-C-induced tube formation in HMVEC-dLy cells in a dose-dependent manner, demonstrating its anti-lymphangiogenic activity in vitro. The results are shown in FIG. 10.

Figure 11:
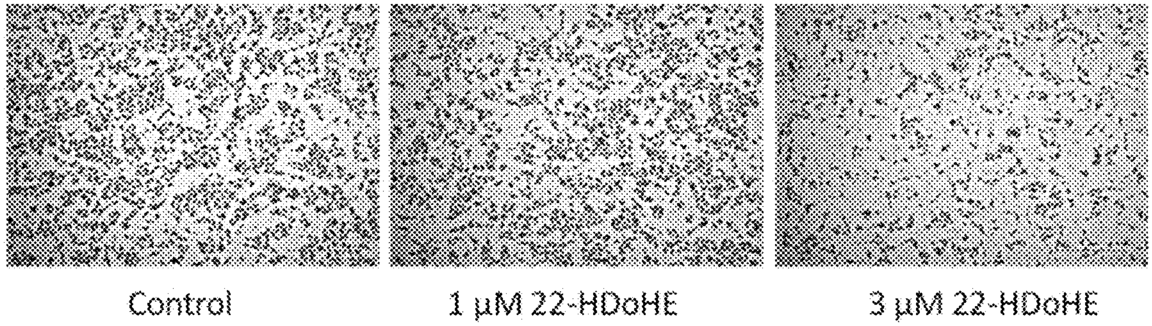
FIG. 11 is a series of photographs showing 22-HDoHE inhibits cellular migration of lymphatic endothelial cells.

The effect of 22-HDoHE on cellular migration of lymphatic endothelial cells was tested, and found it can significantly inhibit complete medium-induced HMVEC-dLy migration in a Boyden chamber assay (FIG. 11).

VIII. REFERENCES

1. Roman, R. J., P-450 metabolites of arachidonic acid in the control of cardiovascular function. Physiol. Rev. 2002, 82 (1), 131-85.
2. Konkel, A.; Schunck, W. H., Role of cytochrome P450 enzymes in the bioactivation of polyunsaturated fatty acids. Biochim. Biophys. Acta 2011, 1814 (1), 210-22.
3. Arnold, C.; Markovic, M.; Blossey, K.; Wallukat, G.; Fischer, R.; Dechend, R.; Konkel, A.; von Schacky, C.; Luft, F. C.; Muller, D. N.; Rothe, M.; Schunck, W. H., Arachidonic acid-metabolizing cytochrome P450 enzymes are targets of {omega}-3 fatty acids. J. Biol. Chem. 2010, 285 (43), 32720-33.
4. (a) Russell, F. D.; Burgin-Maunder, C. S., Distinguishing health benefits of eicosapentaenoic and docosahexaenoic acids. Mar. Drugs 2012, 10 (11), 2535-59; (b) Weintraub, H. S., Overview of prescription omega-3 fatty acid products for hypertriglyceridemia. Postgrad. Med. 2014, 126 (7), 7-18.
5. Wagner, K.; Vito, S.; Inceoglu, B.; Hammock, B. D., The role of long chain fatty acids and their epoxide metabolites in nociceptive signaling. Prostaglandins Other Lipid Mediat. 2014, 113-115, 2-12.
6. Ulu, A.; Stephen Lee, K. S.; Miyabe, C.; Yang, J.; Hammock, B. G.; Dong, H.; Hammock, B. D., An omega-3 epoxide of docosahexaenoic acid lowers blood pressure in angiotensin-II-dependent hypertension. J. Cardiovasc. Pharmacol. 2014, 64 (1), 87-99.
7. Zhang, G.; Panigrahy, D.; Mahakian, L. M.; Yang, J.; Liu, J. Y.; Stephen Lee, K. S.; Wettersten, H. I.; Ulu, A.; Hu, X.; Tam, S.; Hwang, S. H.; Ingham, E. S.; Kieran, M. W.; Weiss, R. H.; Ferrara, K. W.; Hammock, B. D., Epoxy metabolites of docosahexaenoic acid (DHA) inhibit angiogenesis, tumor growth, and metastasis. Proc. Natl. Acad. Sci. U.S.A 2013, 110 (16), 65305.
8. (a) Williams, J. M.; Murphy, S.; Burke, M.; Roman, R. J., 20-hydroxyeicosatetraeonic acid: a new target for the treatment of hypertension. J. Cardiovasc. Pharmacol. 2010, 56 (4), 336-44; (b) Bubb, K. J.; Wen, H.; Panayiotou, C. M.; Finsterbusch, M.; Khan, F. J.; Chan, M. V.; Priestley, J. V.; Baker, M. D.; Ahluwalia, A., Activation of neuronal transient receptor potential vanilloid 1 channel underlies 20-hydroxyeicosatetraenoic acid-induced vasoactivity: role for protein kinase A. Hypertension 2013, 62 (2), 426-33.
9. (a) Bonin, T. F.; Zuccari, D. A.; Jardim-Perassi, B. V.; Ferreira, L. C.; Iskander, A. S.; Varma, N. R.; Shankar, A.; Guo, A. M.; Scicli, G.; Arbab, A. S., HET0016, a selective inhibitor of 20-HETE synthesis, decreases pro-angiogenic factors and inhibits growth of triple negative breast cancer in mice. PLoS One 2014, 9 (12), e116247; (b) Alexanian, A.; Rufanova, V. A.; Miller, B.; Flasch, A.; Roman, R. J.; Sorokin, A., Down-regulation of 20-HETE synthesis and signaling inhibits renal adenocarcinoma cell proliferation and tumor growth. Anticancer Res. 2009, 29 (10), 3819-24.
10. (a) Sporkova, A.; Kopkan, L.; Varcabova, S.; Huskova, Z.; Hwang, S. H.; Hammock, B. D.; Imig, J. D.; Kramer, H. J.; Cervenka, L., Role of cytochrome P-450 metabolites in the regulation of renal function and blood pressure in 2-kidney 1-clip hypertensive rats. Am. J. Physiol. Regul. Integr. Comp. Physiol. 2011, 300 (6), R1468-75; (b) Hoff, U.; Lukitsch, I.; Chaykovska, L.; Ladwig, M.; Arnold, C.; Manthati, V. L.; Fuller, T. F.; Schneider, W.; Gollasch, M.; Muller, D. N.; Flemming, B.; Seeliger, E.; Luft, F. C.; Falck, J. R.; Dragun, D.; Schunck, W. H., Inhibition of 20-HETE synthesis and action protects the kidney from ischemia/reperfusion injury. Kidney Int. 2011, 79 (1), 57-65; (c) Liu, J. Y.; Li, N.; Yang, J.; Li, N.; Qiu, H.; Ai, D.; Chiamvimonvat, N.; Zhu, Y.; Hammock, B. D., Metabolic profiling of murine plasma reveals an unexpected biomarker in rofecoxib-mediated cardiovascular events. Proc. Natl. Acad. Sci. U.S.A 2010, 107 (39), 1701722.
11. Morales-Lazaro, S. L.; Simon, S. A.; Rosenbaum, T., The role of endogenous molecules in modulating pain through transient receptor potential vanilloid 1 (TRPV1). J. Physiol. 2013, 591 (Pt 13), 3109-21.
12. (a) Gopal, V. R.; Jagadeesh, S. G.; Reddy, Y. K.; Bandyopadhyay, A.; Capdevila, J. H.; Falck, J. R., A practical, stereospecific route to 18-, 19-, and 20-hydroxyeicosa-5(Z),8(Z),11(Z),14(Z)-tetraenoic acids (18-, 19-, and 20-HETEs). *Tetrahedron Lett.* 2004, 45 (12), 2563-2565; (b) Proteau-Gagne, A.; St-Jean, F.; Morin, C.; Gendron, L.; Rousseau, E.; Dory, Y. L., Synthesis and Functional Pharmacological Effects on Human Bronchi of 20-Hydroxyeicosatetraenoic Acid. Chem Nat Compd+ 2011, 46 (6), 841-847; (c) Van Bogaert, I.; Zhang, G.; Yang, J.; Liu, J. Y.; Ye, Y.; Soetaert, W.; Hammock, B. D., Preparation of 20-HETE using multifunctional enzyme type 2-negative *Starmerella bombicola*. J. Lipid Res. 2013, 54 (11), 3215-9; (d) Yu, M.; Alonso-Galicia, M.; Sun, C.-W.; J. Roman, R.; Ono, N.; Hirano, H.; Ishimoto, T.; Reddy, Y. K.; Katipally, K. R.; Reddy, K. M.; Gopal, V. R.; Yu, J.; Takhi, M.; Falck, J. R., 20-Hydroxyeicosatetraenoic acid (20-HETE): structural determinants for renal vasoconstriction. Bioorg. Med. Chem. 2003, 11 (13), 2803-2821.

13. Harmon, S. D.; Fang, X.; Kaduce, T. L.; Hu, S.; Raj Gopal, V.; Falck, J. R.; Spector, A. A., Oxygenation of omega-3 fatty acids by human cytochrome P450 4F3B: effect on 20-hydroxyeicosatetraenoic acid production. Prostaglandins, leukotrienes, and essential fatty acids 2006, 75 (3), 169-77.

14. Balas, L.; Durand, T.; Saha, S.; Johnson, I.; Mukhopadhyay, S., Total synthesis of photoactivatable or fluorescent anandamide probes: novel bioactive compounds with angiogenic activity. J. Med. Chem. 2009, 52 (4), 1005-17.

15. (a) KHAN, M. A. J. O. D., Morgan Hill, Calif., 95037, US), WOOD, Paul L. (515 Shawanee Road, Harrogate, Tenn., 37752, US) METHOD FOR THE SYNTHESIS OF DHA. 2012; (b) KHAN AMIN L (US), W. P. L. U., GOODENOWE DAYAN (CA) METHODS FOR THE SYNTHESIS OF 13C LABELED DHA AND USE AS A REFERENCE STANDARD. 2013; (c) Qi, L. W.; Meijler, M. M.; Lee, S. H.; Sun, C. Z.; Janda, K. D., Solid-phase synthesis of anandamide analogues. Organic letters 2004, 6 (10), 1673-1675.

16. Ho, T.-L.; Liu, S.-H., Semihydrogenation of triple bonds in 1-alkene solutions. Synthetic Comm. 1987, 17, 969-973.

17. Wen, H.; Ostman, J.; Bubb, K. J.; Panayiotou, C.; Priestley, J. V.; Baker, M. D.; Ahluwalia, A., 20-Hydroxyeicosatetraenoic acid (20-HETE) is a novel activator of transient receptor potential vanilloid 1 (TRPV1) channel. J. Biol. Chem. 2012, 287 (17), 13868-76.

18. Nilius, B.; Owsianik, G.; Voets, T.; Peters, J. A., Transient receptor potential cation channels in disease. Physiol. Rev. 2007, 87 (1), 165-217.

19. Wang, Y., The functional regulation of TRPV1 and its role in pain sensitization. Neurochem. Res. 2008, 33 (10), 2008-12.

20. Jara-Oseguera, A.; Simon, S. A.; Rosenbaum, T., TRPV1: on the road to pain relief Curr. Mol. Pharmacol. 2008, 1 (3), 255-69.

21. Kaneko, Y.; Szallasi, A., Transient receptor potential (TRP) channels: a clinical perspective. Br. J. Pharmacol. 2014, 171 (10), 2474-507.

22. Gunthorpe, M. J.; Chizh, B. A., Clinical development of TRPV1 antagonists: targeting a pivotal point in the pain pathway. Drug Discov Today 2009, 14 (1-2), 56-67.

23. Yee, J. R.; Kenkel, W.; Caccaviello, J. C.; Gamber, K.; Simmons, P.; Nedelman, M.; Kulkarni, P.; Ferris, C. F., Identifying the integrated neural networks involved in capsaicin-induced pain using fMRI in awake TRPV1 knockout and wild-type rats. Front. Syst. Neurosci. 2015, 9, 15.

24. Wen, H.; Oestman, J.; Bubb, K. J.; Panayiotou, C.; Priestley, J. V.; Baker, M. D.; Ahluwalia, A., 20-Hydroxyeicosatetraenoic Acid (20-HETE) Is a Novel Activator of Transient Receptor Potential Vanilloid 1 (TRPV1) Channel. J. Biol. Chem. 2012, 287 (17), 13868-13876.

25. Sousa-Valente, J.; Andreou, A. P.; Urban, L.; Nagy, I., Transient receptor potential ion channels in primary sensory neurons as targets for novel analgesics. Br. J. Pharmacol. 2014, 171 (10), 250827.

26. Alessandri-Haber, N.; Dina, 0. A.; Chen, X.; Levine, J. D., TRPC1 and TRPC6 channels cooperate with TRPV4 to mediate mechanical hyperalgesia and nociceptor sensitization. J. Neurosci. 2009, 29 (19), 6217-28.

27. Basora, N.; Boulay, G.; Bilodeau, L.; Rousseau, E.; Payet, M. D., 20-hydroxyeicosatetraenoic acid (20-HETE) activates mouse TRPC6 channels expressed in HEK293 cells. J. Biol. Chem. 2003, 278 (34), 31709-16.

28. Conway, S. J., TRPing the switch on pain: an introduction to the chemistry and biology of capsaicin and TRPV1. Chem. Soc. Rev. 2008, 37 (8), 1530-45.

29. Fang, X.; Faraci, F. M.; Kaduce, T. L.; Harmon, S.; Modrick, M. L.; Hu, S.; Moore, S. A.; Falck, J. R.; Weintraub, N. L.; Spector, A. A., 20-Hydroxyeicosatetraenoic acid is a potent dilator of mouse basilar artery: role of cyclooxygenase. Am. J. Physiol. Heart Circ. Physiol. 2006, 291 (5), H2301-7.

30. Folkman, J. Angiogenesis: an organizing principle for drug discovery? Nat Rev Drug Discov 6, 273-286 (2007).

31. Demetri, G. D., et al. Efficacy and safety of regorafenib for advanced gastrointestinal stromal tumours after failure of imatinib and sunitinib (GRID): an international, multicentre, randomised, placebo-controlled, phase 3 trial. Lancet 381, 295-302 (2013).

32. Grothey, A., et al. Regorafenib monotherapy for previously treated metastatic colorectal cancer (CORRECT): an international, multicentre, randomised, placebo-controlled, phase 3 trial. Lancet 381, 303-312 (2013).

33. Llovet, J. M., et al. Sorafenib in advanced hepatocellular carcinoma. N Engl J Med 359, 378-390 (2008).

34. Wu, S., Chen, J. J., Kudelka, A., Lu, J. & Zhu, X. Incidence and risk of hypertension with sorafenib in patients with cancer: a systematic review and meta-analysis. Lancet Oncol 9, 117-123 (2008).

35. Arnold, C., et al. Arachidonic acid-metabolizing cytochrome P450 enzymes are targets of {omega}-3 fatty acids. J Biol Chem 285, 32720-32733 (2010).

36. Zhang, G., Kodani, S. & Hammock, B. D. Stabilized epoxygenated fatty acids regulate inflammation, pain, angiogenesis and cancer. Prog Lipid Res 53, 108-123 (2014).

37. Yang, J.; Schmelzer, K.; Georgi, K.; Hammock, B. D. Quantitative profiling method for oxylipin metabolome by liquid chromatography electrospray ionization tandem mass spectrometry. Anal. Chem. 2009, 81, 8085-8093.

38. Zhengyu, C.; Gerwick, W. H.; Murray, T. F. Antillatoxin is a sodium channel activator that displays unique efficacy in heterologously expressed rNav1.2, rNav1.4 and rNav1.5 α subunits. BMC Neurosci. 2010, 11, 154.

Although the teachings have been described with respect to various embodiments, it should be realized that these teachings are also capable of a wide variety of further and other embodiments within the spirit and scope of the appended claims.

What is claimed is:

1. A method of treating cancer or macular degeneration, the method comprising administering to a subject in need thereof an effective amount of a ω-hydroxylated polyunsaturated fatty acid, or an ester form thereof, or a pharmaceutical composition thereof, wherein the ω-hydroxylated polyunsaturated fatty acid is selected from the group consisting of 20-HEPE, 22-HdoHE, or mixtures thereof.

2. The method of claim 1 wherein the ω-hydroxylated polyunsaturated fatty acid inhibits tumor growth, angiogenesis, lymphangiogenesis, or combinations thereof.

* * * * *